United States Patent
Bonda et al.

(10) Patent No.: US 8,133,477 B2
(45) Date of Patent: *Mar. 13, 2012

(54) DISPERSIONS OF INORGANIC PARTICULATES CONTAINING ALKOXYCRYLENE

(75) Inventors: Craig A. Bonda, Winfield, IL (US); Anna Pavlovic, Elmwood Park, IL (US); Jean Zhang, Hickory Hills, IL (US)

(73) Assignee: Hallstar Innovations Corp., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/554,329

(22) Filed: Sep. 4, 2009

(65) Prior Publication Data
US 2010/0021403 A1   Jan. 28, 2010

Related U.S. Application Data

(60) Continuation-in-part of application No. 12/432,450, filed on Apr. 29, 2009, which is a division of application No. 12/022,758, filed on Jan. 30, 2008, now Pat. No. 7,588,702, which is a continuation-in-part of application No. 11/891,281, filed on Aug. 9, 2007, now Pat. No. 7,597,825.

(51) Int. Cl.
*A61K 8/00* (2006.01)
*A61K 8/18* (2006.01)
*A61Q 17/04* (2006.01)
*F21V 9/04* (2006.01)
*F21V 9/06* (2006.01)
*G02B 5/22* (2006.01)
*G02B 5/26* (2006.01)

(52) U.S. Cl. ............ 424/59; 252/589; 424/60; 424/401; 424/94.1; 514/337; 514/532; 514/557; 514/569; 514/703; 524/90; 558/410; 546/280.1; 560/61; 562/471; 562/490; 562/510; 568/446; 568/823

(58) Field of Classification Search ............ 424/59, 424/60, 94.1; 558/410; 560/81, 61; 568/446; 568/823; 562/510, 471, 490; 546/280.1; 514/569, 337, 532, 557, 703, 729; 252/589
See application file for complete search history.

(56) References Cited

U.S. PATENT DOCUMENTS

| | | |
|---|---|---|
| 2,623,060 A | 12/1952 | Cragoe |
| 3,215,724 A | 11/1965 | Strobel et al. |
| 3,337,357 A | 8/1967 | Strobel et al. |
| 4,284,621 A | 8/1981 | Preuss et al. |
| 4,293,542 A | 10/1981 | Lang et al. |
| 4,307,240 A | 12/1981 | Ching |
| 4,396,240 A | 8/1983 | Henson |
| 4,562,278 A | 12/1985 | Hill |
| 4,617,374 A | 10/1986 | Pruett et al. |
| 4,707,537 A | 11/1987 | Pruett et al. |
| 5,576,354 A | 11/1996 | Deflandre et al. |
| 5,663,213 A | 9/1997 | Jones et al. |
| 5,738,842 A | 4/1998 | Raspanti et al. |
| 5,783,307 A | 7/1998 | Fagerburg et al. |
| 5,989,528 A | 11/1999 | Tanner et al. |
| 5,993,789 A | 11/1999 | Bonda et al. |
| 6,113,931 A | 9/2000 | Bonda et al. |
| 6,225,052 B1 | 5/2001 | Batz et al. |
| 6,284,916 B1 | 9/2001 | Bonda et al. |
| 6,485,713 B1 | 11/2002 | Bonda et al. |
| 6,518,451 B2 | 2/2003 | Bonda et al. |
| 6,537,529 B1 | 3/2003 | Bonda |
| 6,551,605 B2 | 4/2003 | Bonda |
| 6,800,274 B2 | 10/2004 | Bonda et al. |
| 6,890,521 B2 | 5/2005 | Bonda |

(Continued)

FOREIGN PATENT DOCUMENTS

DE   1222926   8/1966

(Continued)

OTHER PUBLICATIONS

*Amoco® NDC for Coatings, Inks and Adhesives*, Amoco Chemicals, Bulletin FA-21b.
*Light Absorbing Properties of Naphthalate Containing Polyesters*, BP p.l.c. Technical Bulletin N-10 (2001).
Baussard, "Chap. II: Donor-Acceptor pairs for Forster Resonance Energy Transfer (FRET)" in *Synthesis of New Ionic Functional Polymers by Free Radical Polymerization via the RAFT Process*, Dissertation, Catholic University of Louvain, (Jan. 26, 2004).

(Continued)

*Primary Examiner* — Mark Kopec
*Assistant Examiner* — Bijan Ahvazi
(74) *Attorney, Agent, or Firm* — Marshall, Gerstein & Borun LLP

(57) ABSTRACT

A composition comprising an inorganic particulate material in an amount of about 20 wt % to about 70 wt %, a carrier for the particulate material comprising a compound of formula (I) in an amount of about 1 wt % to about 70 wt %, a particulate material coating material in an amount of about 0 wt % to about 5 wt %, and a dispersing agent for the particulate material in an amount of about 0 wt % to about 5 wt %, based on the total weight of the composition,

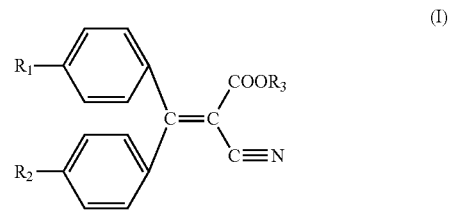

(I)

wherein one of $R_1$ and $R_2$ is a straight or branched chain $C_1$-$C_{30}$ alkoxy radical, and the non-alkoxy $R_1$ or $R_2$ is hydrogen; and $R_3$ is a straight or branched chain $C_1$-$C_{30}$ alkyl radical.

32 Claims, No Drawings

U.S. PATENT DOCUMENTS

| | | |
|---|---|---|
| 6,899,866 B2 | 5/2005 | Bonda |
| 6,905,525 B2 | 6/2005 | Wood et al. |
| 6,919,473 B2 | 7/2005 | Bonda et al. |
| 6,962,692 B2 | 11/2005 | Bonda et al. |
| 7,064,114 B2 | 6/2006 | Yiv et al. |
| 7,201,893 B2 | 4/2007 | Wendel et al. |
| 7,235,587 B2 | 6/2007 | Bonda et al. |
| 7,292,156 B2 | 11/2007 | Smith et al. |
| 7,449,698 B2 | 11/2008 | Nguyen et al. |
| 7,534,420 B2 | 5/2009 | Bonda et al. |
| 2002/0127192 A1 | 9/2002 | Murphy et al. |
| 2003/0176542 A1* | 9/2003 | Abe et al. ............... 524/91 |
| 2004/0047817 A1 | 3/2004 | Bonda |
| 2004/0057914 A1* | 3/2004 | Bonda et al. ............ 424/59 |
| 2004/0170579 A1 | 9/2004 | Mobius |
| 2005/0053571 A1* | 3/2005 | Hanada et al. ........ 424/70.122 |
| 2006/0062746 A1* | 3/2006 | Brillouet et al. ........ 424/59 |
| 2006/0228311 A1 | 10/2006 | Bonda et al. |
| 2008/0286217 A1 | 11/2008 | Chaudhuri et al. |
| 2009/0057627 A1* | 3/2009 | Bonda et al. ........... 252/601 |
| 2009/0246157 A1* | 10/2009 | Bonda et al. ............ 424/60 |

FOREIGN PATENT DOCUMENTS

| | | |
|---|---|---|
| EP | 0570838 | 11/1993 |
| EP | 0761201 | 3/1997 |
| EP | 1323743 | 7/2003 |
| JP | 08225672 | 9/1996 |
| JP | 2005139263 | 6/2005 |
| SU | 1273360 | 11/1986 |
| WO | WO-00/27337 | 5/2000 |
| WO | WO-02/42368 | 5/2002 |
| WO | WO-2007/128840 | 11/2007 |

OTHER PUBLICATIONS

Bonda, "Research pathways to photostable sunscreens," *Cosmetics & Toiletries Magazine*, 123:1, 49-60 (Feb. 5, 2008).

Chatelain et al., "Photostabilization of butyl methoxydibenzoylmethane (Avobenzone) and ethylhexyl methoxycinnamate by bis-ethylhexyloxyphenol methoxyphenyl triazine (Tinosorb S), a new UV broadband filter", *Photochemisty and Photobiology*, 74(3):401-6 (2003).

Cheung, "Photophysical processes in dimethyl 2,6-naphthalenedicarboxylate and poly(ethylene 2,6-naphthalenedicarboxylate)" *J. Polymer Sci.: Polymer Let. Ed.*, 17:227-32 (1979).

European Search Report EP 08103204.7, dated Jul. 25, 2008.

European Search Report for EP 08 10 3205, dated Jul. 14, 2008.

Horiba Jobin Yvon Ltd., *A Guide to Recording Fluorescence Quantum Yields*, www.jyhoriba.co.uk.

International Search Report and Written Opinion fo PCT/US/2008/058454, dated Sep. 23, 2008.

International Search Report and Written Opinion for PCT/US2008/058456, dated Jun. 27, 2008.

Karitzky et al., "Synthesis of 3,3-diarylpyrrolidines from diaryl ketones", *ARKIVOC*, (Gainesville, FL, United States), 5:9-18 (2003) URL: http://arkatusa.org/zark/journal/2003/Bernath/GB-594J/594J.pdf.

Min et al., "Spectroscopic studies on the interaction of cinnamic acid and its hydroxyl derivatives with human serum albumin", *J. Mol. Structure*, 692:71-80 (2004).

Palm et al., "Update on photoprotection" *Dermatologic Therapy*, 20:360-76 (2007).

Senchenya et al., "Silicon-containing esters of $\alpha$-cyanoacrylic acid: synthesis and properties", *Russian Chem. Bul.*, 42:909-11 (1993).

Somsen et. al., "Planar chromatography coupled with spectroscopic techniques", *J. Chromatography A*, 703:613-65 (1995).

Turro et al., *Modern Molecular Photochemistry*, Chapter 9, University Science Books (1991).

* cited by examiner

DISPERSIONS OF INORGANIC PARTICULATES CONTAINING ALKOXYCRYLENE

CROSS REFERENCE TO RELATED APPLICATIONS

This application is a continuation-in-part of U.S. application Ser. No. 12/432,450 filed on Apr. 29, 2009, which is a divisional of U.S. application Ser. No. 12/022,758 filed Jan. 30, 2008, which is a continuation-in-part of U.S. application Ser. No. 11/891,281 filed Aug. 9, 2007. The entire text of the priority applications are incorporated herein by reference in their entirety.

FIELD OF THE INVENTION

The present invention is directed to dispersions comprising particulate materials, preferably inorganic particulate materials in an alkoxycrylene carrier, and compositions, preferably sunscreen or dermatological formulations, comprising said dispersions. More particularly, the present invention is directed to sunscreen or dermatological formulations comprising dispersions of zinc oxide or titanium dioxide using an alkoxycrylene compound as the carrier.

BACKGROUND

A sunscreen composition is a topical product comprising one or more UV filter compounds that absorb, scatter, and/or reflect some of the sun's ultraviolet radiation on the skin when it is exposed to sunlight. The UV filter compound(s) can be classified into three groups: chromophore-containing organic compounds such as para-aminobenzoic acid (PABA), organic particulates such as such as methylene bis-benzotriazolyl tetramethylbutylphenol (TINOSORB M by CIBA®), and inorganic particulates such as kaolin, talc, and metal oxides (e.g. zinc oxide, titanium dioxide).

Inorganic particulates are physical-barrier UV filters that reflect both UV-A and UV-B rays. Inorganic particulates offer the broadest protection against UV rays (i.e. below 290 nm to around 380 nm) that no single organic UV absorber can match. In addition, inorganic particulates provide high sun protection factors (SPFs), are economical to use, are completely stable on exposure to sunlight if properly treated, and do not cause skin problems because they are not absorbed into the skin.

As shown in this assignee's pending application Ser. Nos. 11/891,281 and 12/022,758 filed on Aug. 9, 2007 and Jan. 30, 2008, respectively, the disclosures of which are hereby incorporated by reference, it has been found that alkoxy substituted α-cyano-β, β-diphenylacrylates (alkoxycrylenes), particularly methoxycrylenes, return chromophore-containing UV filter agents, particularly butyl methoxydibenzoylmethane (Avobenzone), octyl methoxycinnamate (Octinoxate), and octyl salicylate (Octisalate), from both an electronically excited singlet state and excited triplet state back to their ground state, thereby photostabilizing the UV-absorbing organic molecules.

Chromophore-containing UV filter agents work by absorbing ultraviolet light. The absorption of ultraviolet light by a chromophore-containing organic molecule causes the excitation of an electron in the chromophore moiety from an initially occupied, low energy orbital to a higher energy, previously unoccupied orbital. The energy of an absorbed photon is used to energize an electron and cause it to "jump" to a higher energy orbital, see Turro, Modern Molecular Photochemistry, 1991. Two excited electronic states derive from the electronic orbital configuration produced by UV light absorption. In one state, the electron spins are paired (antiparallel) and in the other state the electron spins are unpaired (parallel). The state with paired spins has no resultant spin magnetic moment, but the state with unpaired spins possesses a net spin magnetic moment. A state with paired spins remains a single state in the presence of a magnetic field, and is termed a singlet state. A state with unpaired spins interacts with a magnetic field and splits into three quantized states, and is termed a triplet state.

In the electronically excited state, the chromophore-containing organic molecule is prone to degrade via a number of known pathways and, therefore, can absorb little or no additional UV light, see Bonda, Cosmetics & Toiletries 123(2):1-11, (2008). To photostabilize an electronically excited chromophore-containing organic molecule in order to provide sufficient UV protection, it must be returned to the ground state before it undergoes a photochemical reaction destructive to its UV absorbing capability. Unlike the alkoxycrylene compounds that were unexpectedly found to be capable of quenching both excited singlet state energy and excited triplet state energy, other known photostabilizing sunscreen additives, such as octocrylene, methylbenzilydene camphor, and the esters or polyesters of naphthalene dicarboxylic acid of this assignee's U.S. Pat. Nos. 6,113,931; 6,284,916; 6,518,451; and 6,551,605, all hereby incorporated by reference, are only capable of quenching excited triplet state energy.

SUMMARY

The photostabilizing electronic excited state energy—particularly singlet state energy from a UV-absorbing molecule—has been found to be readily transferred to (accepted by) α-cyanodiphenylacrylate compounds having an alkoxy radical in the four (para) position (hereinafter "alkoxycrylenes") on one of the phenyl rings having the formula (I):

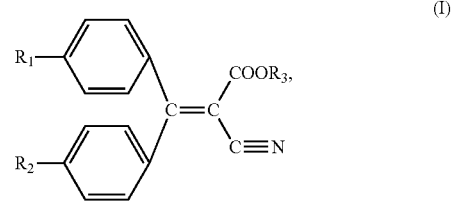

wherein one of $R_1$ and $R_2$ is a straight or branched chain $C_1$-$C_{30}$ alkoxy radical, preferably $C_1$-$C_8$, more preferably methoxy, and the non-alkoxy radical $R_1$ or $R_2$ is hydrogen; and $R_3$ is a straight or branched chain $C_1$-$C_{30}$ alkyl radical, preferably $C_2$-$C_{20}$.

It has surprisingly been found that when metal oxides, particularly attenuation-grade metal oxides, are combined in a dispersion with an alkoxycrylene compound as the carrier, the performance of a resulting sunscreen or dermatological formulation that comprises the dispersion is enhanced well beyond what would be expected by a purely additive effect. Sunscreen or dermatological formulations comprising dispersions of attenuation-grade metal oxides and alkoxycrylene compounds unexpectedly have about 30% to about 66% higher SPF values and about 28%+ higher UVA-PF values than would result in sunscreen or dermatological formulations comprising only attenuation-grade metal oxides in a non-alkoxycrylene carrier.

DETAILED DESCRIPTION OF THE PREFERRED EMBODIMENTS

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The term "alkoxy" herein refers to a radical extending from the para position of one or both of the phenyl rings having the formula O—R, wherein R is an alkyl radical, straight chain or branched having 1 to 30 carbon atoms, preferably wherein R is $C_1$ to $C_8$, more preferably $C_2$-$C_{20}$, and most preferably —O—$CH_3$ (methoxy). The oxygen atom of the alkoxy radical is covalently bonded to the para carbon atom of one of the phenyl rings, preferably having the formula (II) or (III):

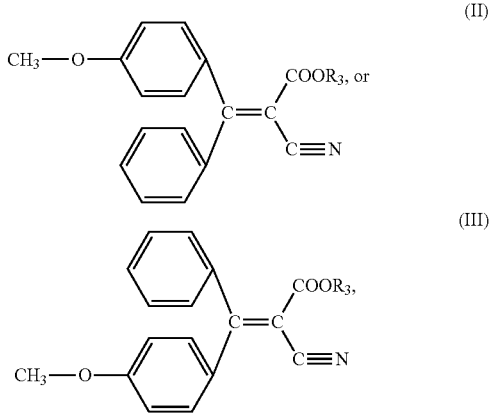

wherein $R_3$ is as previously defined.

The term "crylene" as used herein refers to a chromophoric moiety that includes an α-cyano-β,β-diphenyl propanoic acid ester.

The term "cyano" as used herein refers to a —C≡N group, also designated "—CN."

The abbreviations used herein are defined in Table 1.

TABLE 1

Abbreviations

| Abbreviation | Name |
|---|---|
| BHB | Butyloctyl salicylate |
| EHMC | Ethylhexyl methoxycrylene |
| INCI | International Nomenclature of Cosmetic Ingredients |
| PEG | Poly(ethylene glycol) |
| SPF | Sun protection factor |
| UV | Ultraviolet |
| UVA-PF | UVA-Protection factor |
| UVR | Ultraviolet radiation |

The dispersions described herein comprise a combination of an inorganic particulate material, particularly a metal oxide, and a carrier for the inorganic particulate material comprising a compound of formula (I). The carrier for the inorganic particulate material can further comprise one or more additional carriers. The dispersions described herein can further comprise one or more additional particulate materials such as latex particles and/or organic pigments. The dispersions described herein can also be formulated to further comprise one or more coating materials for the inorganic particulate material and/or one or more dispersing agents for the inorganic particulate material. The dispersions described herein can optionally be combined with one or more UV-A photoactive compounds and/or one or more UV-B photoactive compounds. The photoactive compounds can be photodegradable compounds that reach an electronic singlet excited state upon exposure to UV radiation. Examples of photoactive compounds that can be combined with the dispersions described herein include dibenzoylmethane derivatives (e.g. Avobenzone), octyl methoxycinnamate (octinoxate), and octyl salicylate (octisalate), particularly a combination thereof. The dispersions described herein can also optionally be combined with one or more photostabilizing compounds such as oxybenzone, octocrylene, methylbenzilydene camphor, and naphthalene dicarboxylate esters. The dispersions described herein can also optionally be combined with a water soluble UV filter compound, such as sulfonated UV filters, and/or a hydroxybenzophenone compound. The dispersions described herein can also optionally be combined with a benzotriazole compound such as 2,2'-methylenebis(6-(2H-benzotriazol-2-yl)-4-(1,1,3,3-tetramethylbutyl)phenol) (Tinsosorb®), and/or a triazine compound. The dispersions described herein can further optionally be combined with one or more of the following: antioxidants (e.g. vitamin E derivatives, vitamin A derivatives), natural active ingredients (e.g. creatine, taurine), known anti-wrinkle ingredients (β-alanine), hydrophilic skin care ingredients (e.g. water-soluble antioxidants, vitamins), lipophilic active ingredients (e.g. ubiquinones, retinoids, and carotinoids), and UV-sensitive active ingredients.

Dispersions comprising inorganic particulates are excellent sunscreen agents because they offer a broad range of protection from both UV-A and UV-B rays. However, the manufacture of these dispersions is often difficult. Inorganic particulates exist as particle aggregates (i.e. two or more crystals that have bonded irreversibly together during the manufacture process) instead of as individual crystals. During the manufacture of inorganic particulate dispersions, groups of the particle aggregates often stick together to form agglomerates. Agglomerates, which act like individual large particles, are less transparent than aggregates, causing undesired whitening when applied to the skin, and reflect UV rays less efficiently than the same mass of smaller particles. To take advantage of the broad range of UV protection that inorganic particulates can provide, their manufacturing process must prevent significant formation of agglomerates. For example zinc oxide, a widely used inorganic particulate in sunscreen and dermatological formulations, has been found to be the most effective when its particles are manufactured to be less than 0.2 micrometers across. Zinc oxide particles in the range of 0.1 to 0.2 micrometers provide the best combination of attenuation and aesthetics because they are fine enough to appear almost completely transparent, yet effective across the full UV spectrum.

Commonly assigned pending application Ser. Nos. 11/891,281 and 12/022,758 filed on Aug. 9, 2007 and Jan. 30, 2008, respectively, describe a method of photostabilizing a photon-excited photoactive compound that reaches a singlet excited state when exposed to UV radiation in a sunscreen or dermatological formulation. The method comprises the steps of mixing the photoactive compound with a compound of formula (I) and exposing the mixture to UV radiation in an amount sufficient for the photoactive compound to reach an electronic singlet excited state. The compound of formula (I) accepts the singlet excited state energy from the excited photoactive compound, allowing the photoactive compound to return to its ground state so that it is capable of absorbing additional UV radiation before undergoing a photochemical reaction destructive to its UV-absorbing capability. Thus, the singlet excited state energy from the photon-excited photoactive compound is quenched through transfer from the photon-excited photoactive compound to the compound of formula (I), thereby photostabilizing the photoactive compound.

It has surprisingly been found that when metal oxides, particularly attenuation-grade metal oxides, are combined in a dispersion with an alkoxycrylene compound of formula (I) as the carrier, the performance of a resulting sunscreen or dermatological formulation that comprises the dispersion is enhanced well beyond what would be expected by a purely additive effect. Sunscreen or dermatological formulations comprising the dispersions of metal oxides, particularly attenuation-grade metal oxides, in an alkoxycrylene carrier unexpectedly have about 30% to about 66% higher SPF values and about 28%+ higher UVA-PF values than would result in sunscreen or dermatological formulations comprising only attenuation-grade metal oxides without the alkoxycrylene compound. It has also surprisingly been found that the degree of enhancement of a sunscreen or dermatological formulation that comprises the dispersions described herein increases with the concentration of the alkoxycrylene compound in the dispersion. For example, sunscreen formulations comprising the metal oxide dispersions described herein comprising 3.4% or 1.7% by weight of an alkoxycrylene compound of formula (I), based on the total weight of the sunscreen formulation, have SPF values of 17 and 10, respectively.

In accordance with one important aspect of the invention, an alkoxycrylene compound of formula (I) is used as a carrier in a dispersion comprising a particulate material, preferably a UV filter substance,

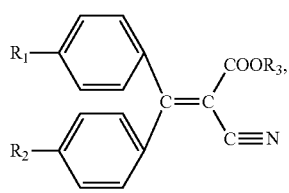

(I)

wherein one of $R_1$ and $R_2$ is a straight or branched chain $C_1$-$C_{30}$ alkoxy radical, preferably $C_1$-$C_8$, more preferably methoxy, and the non-alkoxy radical $R_1$ or $R_2$ is hydrogen; and $R_3$ is a straight or branched chain $C_1$-$C_{30}$ alkyl radical, preferably $C_2$-$C_{20}$.

The carrier makes up the bulk of the non-particulate UV filter substance in a dispersion. Preferably, the carrier is dermatologically suitable (i.e. does not cause or promote adverse reactions upon the skin). Compounds that commonly function as carriers include silicones, synthetics esters and oils, natural esters and oils, and hydrocarbons. Some suitable carriers include vegetable oils, for example, fatty acid glycerides, fatty acid esters, and fatty alcohols. Specific examples include cyclopentasiloxane, capric/caprylic triglycerides, isononyl isononanoate, Simmondsia chinensis (Jojoba) seed oil, Helianthus annus (Sunflower) seed oil, isododecane, oleic and linoleic glycerides, oleyl alcohol, isopropyl palmitate, pentaerythritol tetracaprylate/caprate, pentaerythritol tetraisostearate, triethoxysilylethyl polydimethylsiloxyethyl hexyl dimethicone, caprylyl methicone, Ricinus communis (Castor) seed oil, Jojoba esters, mineral oil, isopropyl myristate, acrylic polymers, butyloctyl salicylate, and C12-C15 alkyl benzoates. In the dispersion of the invention, the carrier is an alkoxycrylene compound of formula (I) and may or may not include one or more additional carriers, such as those identified above. In one specific embodiment of the invention, the carrier is a methoxycrylene compound. For example, the carrier is ethylhexyl methoxycrylene (EHMC, SOLASTAY™ $S_1$). In some embodiments, the alkoxycrylene carrier is combined with one or more additional carriers such as a C12-C15 alkylbenzoate and/or butyloctyl salicylate.

The amount of the alkoxycrylene carrier need only be sufficient to provide a uniform dispersion of the inorganic particles when they are applied to the skin to ensure adequate coverage of the skin with the UV filter material. In one embodiment, the alkoxycrylene carrier is present in the dispersion in an amount in the weight range of about 1% to about 70% by weight, based on the total weight of the dispersion. In another embodiment, the alkoxycrylene carrier is present in the dispersion in an amount in the weight range of about 10% to about 40% by weight, based on the total weight of the dispersion. When an additional carrier, such as a C12-C15 alkyl benzoate and/or butyloctyl salicylate, is combined with the dispersion, the additional carrier is present in an amount in the weight range of about 0% to about 35% by weight, preferably about 1% to about 35% by weight, more preferably about 10% to about 25% by weight, based on the total weight of the dispersion.

Preferred particulate UV filter substances for the purposes of the dispersion of the preferred embodiment are inorganic particulates, especially metal oxides and/or other metal compounds which are slightly soluble or insoluble in water, especially oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals, and mixtures of such oxides, and the sulfate of barium ($BaSO_4$). The metal oxides are preferably micronized (i.e. small particles having a particle size in the range of about 100 nm to about 370 nm.

Zinc oxide particles and predispersions of zinc oxide particles which are suitable according to the invention are distinguished by a primary particle size of <300 nm and can be obtained under the following proprietary names from the stated companies:

| Proprietary name | ZnO Coating | Manufacturer |
|---|---|---|
| Z-Cote HP1 | 2% Dimethicone Triethoxycaprylyl silane | BASF |
| Z-Cote | / | BASF |
| ZnO NDM | 5% Dimethicone | H&R |
| ZnO Neutral | / | H&R |
| MZ-300 | / | Tayca Corporation |
| MZ-500 | / | Tayca Corporation |
| MZ-700 | / | Tayca Corporation |
| MZ-303S | 3% Methicone | Tayca Corporation |
| MZ-505S | 5% Methicone | Tayca Corporation |
| MZ-707S | 7% Methicone | Tayca Corporation |
| MZ-303M | 3% Dimethicone | Tayca Corporation |
| MZ-505M | 5% Dimethicone | Tayca Corporation |
| MZ-707M | 7% Dimethicone | Tayca Corporation |
| Z-Sperse Ultra | ZnO (>=56%)/Ethylhexyl Hydroxystearate Benzoate/ Dimethicone/Cyclomethicone | Collaborative Laboratories |
| Samt-UFZO-450/D5 (60%) | ZnO (60%)/ Cyclomethicone/Dimethicone | Miyoshi Kasei |

Particularly preferred zinc oxides for the purposes of the invention are Z-Cote HP1 and Z-Cote from BASF and zinc oxide NDM from Haarmann & Reimer.

Zinc oxides and other metal oxides are chemically and catalytically reactive. These metal oxide particles may advantageously be surface-treated ("coated"), the intention being, for example, to form or retain a hydrophilic, amphiphilic or hydrophobic character, and to reduce the reactivity and/or catalytic activity of the metal oxide. This surface treatment may consist of coating the particles by processes known per se with a thin hydrophilic and/or hydrophobic inorganic and/or organic layer. The various surface coatings may also contain water.

or alginic acid. These organic and organosilane surface coatings may occur alone, in combination and/or in combination with inorganic coating materials. The coatings usually comprise about 0 wt % to about 10 wt %, preferably about 1 wt % to about 10 wt %, based on the total weight of the compositions described herein.

The metal oxides of the dispersions described herein may be treated with silane surface coatings such as triethoxycaprylylsilane. Suitable silane coatings for the purposes of the present invention are obtainable under the following proprietary names from Kobo Products:

| Trade Name | INCI Name | Product Type |
| --- | --- | --- |
| BRO-11S2 | Iron Oxides (C.I. 77491) (And) Triethoxycaprylylsilane | Red Iron Oxide |
| BYO-11S2 | Iron Oxides (C.I. 77492) (And) Triethoxycaprylylsilane | Yellow Iron Oxide |
| BBO-11S2 | Iron Oxides (C.I. 77499) (And) Triethoxycaprylylsilane | Black Iron Oxide |
| BLACK NF-11S2 | Iron Oxides (C.I. 77499) (And) Triethoxycaprylylsilane | Black Iron Oxide |
| BUB-11S2 | Ultramarines (And) Triethoxycaprylylsilane | Ultramarine Blue |
| BUV CG-11S2 | Ultramarines (And) Triethoxycaprylylsilane | Ultramarine Violet |
| BHG TM-11S2 | Chromium Hydroxide Greens (And) Triethoxycaprylylsilane | Green Chromium Hydroxide |
| BCO-11S2 | Chromium Oxide Greens (And) Triethoxycaprylylsilane | Green Chromium Oxide |
| BTD-11S2 | Titanium Dioxide (And) Triethoxycaprylylsilane | Pigmentary Titanium Dioxide |
| RBTD-11S2P | Titanium Dioxide (And) Triethoxycaprylylsilane | Pigmentary Titanium Dioxide |
| RBTD-671-11S2 | Titanium Dioxide (And) Triethoxycaprylylsilane | Pigmentary Titanium Dioxide |
| A120-ZNO-11S3 | Zinc Oxide (And) Triethoxycaprylylsilane | Zinc Oxide |
| Red 33AL-11S2 | Red 33 Lake (And) Triethoxycaprylylsilane | D&C Red 33 Aluminum Lake |
| Yellow 5AL-11S2 | Yellow 5 Lake (And) Triethoxycaprylylsilane | FD&C Yellow 5 Aluminum Lake |
| Yellow 6AL-11S2 | Yellow 6 Lake (And) Triethoxycaprylylsilane | FD&C Yellow 6 Aluminum Lake |
| Red 6SS-11S2 | Red 6 (And) Triethoxycaprylylsilane | D&C Red 6 |
| Red 6BA C-11S5 | Red 6 Lake (And) Triethoxycaprylylsilane | D&C Red 6 Barium Lake |
| Red 7CA C-11S5 | Red 7 Lake (And) Triethoxycaprylylsilane | D&C Red 7 Calcium Lake |
| ZnO XZ-11S3 | Zinc Oxide (And) Triethoxycaprylylsilane | Attenuation Grade Zinc Oxide |
| ZnO FSF-11S4 | Zinc Oxide (And) Triethoxycaprylylsilane | Attenuation Grade Zinc Oxide |
| ZnO-USP1-11S3 | Zinc Oxide (And) Triethoxycaprylylsilane | Attenuation Grade Zinc Oxide |
| GMS-11S2 | Mica (And) Triethoxycaprylylsilane | Sericite |
| MICA S- 11S4 | Mica (And) Triethoxycaprylylsilane | Mica |
| TALC U-11S2 | Talc (And) Triethoxycaprylylsilane | Talc |

Inorganic surface coatings for the purposes of the present invention may consist of oxides or hydrous oxides such as, for example, aluminum oxide ($Al_2O_3$), aluminum hydroxide $Al(OH)_3$ or aluminum oxide hydrate (also: alumina, CAS No.: 1333-84-2), sodium hexametaphosphate $(NaPO_3)_6$, sodium metaphosphate $(NaPO_3)_n$, silicon dioxide ($SiO_2$) (also: silica, CAS No.: 7631-86-9) or iron oxide ($Fe_2O_3$). These inorganic surface coatings may occur alone, in combination and/or in combination with organic coating materials.

Organic surface coatings for the metal oxide particles of the dispersions described herein may consist of polyols, amines or alkanolamines, vegetable or animal aluminum stearate, vegetable or animal stearic acid, lauric acid, dimethylpolysiloxane (also: dimethicones), methylpolysiloxane (methicones), simethicones (a mixture of dimethylpolysiloxane with an average chain length of from 200 to 350 dimethylsiloxane units and silica gel) triethoxycaprylylsilane, and/

Titanium dioxide particles, when incorporated into the dispersions described herein, may be in the form of both the rutile and anatase crystal modification and may advantageously be surface-treated ("coated"). Often titanium dioxide is coated using Alumina added immediately after the titanium dioxide crystals have formed. Coated and uncoated titanium dioxides may be used in the form of commercially available oily or aqueous predispersions. It may be advantageous to add dispersion aids and/or solubilization mediators, together with the $TiO_2$ and alkoxycrylene dispersions described herein, in typical amounts of about 0 wt % to about 10 wt %, preferably about 1 wt % to about 3 wt %, based on the total weight of the composition.

Suitable titanium dioxide particles and predispersions of titanium dioxide particles for the dispersions described herein are obtainable under the following proprietary names from the stated companies:

| Proprietary name | Coating | Additional ingredients of the predispersion | Manufacturer |
| --- | --- | --- | --- |
| MT-150W | None | — | Tayca Corporation |
| MT-150A | None | — | Tayca Corporation |
| MT-500B | None | — | Tayca Corporation |
| MT-600B | None | — | Tayca Corporation |
| MT-100TV | Aluminum hydroxide Stearic acid | — | Tayca Corporation |
| MT-100Z | Aluminum hydroxide Stearic acid | — | Tayca Corporation |
| MT-100T | Aluminum hydroxide Stearic acid | — | Tayca Corporation |
| MT-500T | Aluminum hydroxide Stearic acid | — | Tayca Corporation |
| MT-100S | Aluminum hydroxide Lauric acid | — | Tayca Corporation |
| MT-100F | Stearic acid Iron oxide | — | Tayca Corporation |
| MT-100SA | Alumina Silica | — | Tayca Corporation |
| MT-500SA | Alumina Silica | — | Tayca Corporation |
| MT-600SA | Alumina Silica | — | Tayca Corporation |
| MT-100SAS | Alumina Silica Silicone | — | Tayca Corporation |
| MT-500SAS | Alumina Silica Silicone | — | Tayca Corporation |
| MT-500H | Alumina | — | Tayca Corporation |
| MT-100AQ | Silica Aluminum hydroxide Alginic acid | — | Tayca Corporation |
| Eusolex T | Water Simethicone | — | Merck KgaA |
| Eusolex T-2000 | Alumina Simethicone | — | Merck KgaA |
| Eusolex T-Olio F | Silica Dimethylsilate Water | $C_{12-15}$ Alkylbenzoate Calcium Poly-hydroxystearate Silica Dimethylsilate | Merck KgaA |
| Eusolex T-Olio P | Water Simethicone | Octyl Palmitate PEG-7 Hydrogenated Castor Oil Sorbitan Oleate Hydrogenated Castor Oil Beeswax Stearic acid | Merck KgaA |
| Eusolex T-Aqua | Water Alumina Sodium metaphosphate | Phenoxyethanol Sodium Methylparabens Sodium metaphosphate | Merck KgaA |
| Eusolex T-45D | Alumina Simethicone | Isononyl Isononanuate Polyglyceryl Ricinoleate | Merck KgaA |
| Kronos 1171 (Titanium dioxide 171) | None | — | Kronos |
| Titanium dioxide P25 | None | — | Degussa |
| Titanium dioxide T805 | Octyltri-methylsilane (Uvinul $TiO_2$) | — | Degussa |
| UV-Titan X610 | Alumina Dimethicone | — | Kemira |
| UV-Titan X170 | Alumina Dimethicone | — | Kemira |
| UV-Titan X161 | Alumina Silica Stearic acid | — | Kemira |

-continued

| Proprietary name | Coating | Additional ingredients of the predispersion | Manufacturer |
| --- | --- | --- | --- |
| UV-Titan M210 | Alumina | — | Kemira |
| UV-Titan M212 | Alumina | Glycerol | Kemira |
| UV-Titan M262 | Alumina Silicone | — | Kemira |
| UV-Titan M160 | Alumina Silica Stearic acid | — | Kemira |
| Tioveil AQ 10PG | Alumina Silica | Water Propylene glycol | Solaveil Uniquema |
| Mirasun TiW 60 | Alumina Silica | Water | Rhone-Poulenc |

The titanium dioxides of the preferred dispersions described herein are distinguished by a primary particle size between about 10 nm to about 150 nm.

Titanium dioxide particles particularly preferred for the purposes of the dispersions described herein are MT-100 Z and MT-100 TV from Tayca Corporation, Eusolex T-2000 from Merck and titanium dioxide T 805 from Degussa.

In one embodiment, the titanium dioxide particles of the dispersion are uncoated and doped with low levels of manganese, e.g. about 0.1 wt % to about 5 wt %, preferably 0.3 wt % to about 1 wt % (e.g. 0.67 wt %), based on the total weight of the $TiO_2$ particles, after doping. Low-level inclusion of manganese or some other transition metal ions into $TiO_2$ particles introduces extra energy levels into the titanium dioxide, which are present in the UVA portion of the ultraviolet spectrum. The uncoated manganese-doped titanium dioxide particles deliver a broad spectrum of UV-A and UV-B protection, act as free radical scavengers, enhance the photostability of other UV active compounds in the resulting formulation, and help to avoid whitening on skin.

The coated metal oxides of another embodiment may also be used in various combinations with other coated or uncoated metal oxides, for example coated zinc oxide with coated or uncoated titanium dioxide particles. Such combinations may be provided in any selected weight ratio of coated/coated or coated/uncoated metal oxide in the range of 1:10 to 10:1, for example.

Latex particles are other advantageous particles that can be included in the dispersions described herein. Latex particles which are particularly advantageous are described in the following publications: U.S. Pat. No. 5,663,213 and EP 0 761 201. One example of particularly advantageous latex particles are those formed from water and styrene/acrylate copolymers and available for example under the proprietary name "Alliance SunSphere" from Rohm & Haas.

An advantageous organic pigment, 2,2'-methylenebis(6-(2H-benzotriazol-2-yl)-4-(1,1,3,3-tetramethylbutyl-)phenol) (INCI: bis-octyltriazol), which is obtainable under the proprietary name Tinosorb® M from CIBA-Chemikalien GmbH, can also be included in one embodiment of the dispersions described herein.

In another embodiment, the dispersions may further comprise a dispersant in typical amounts of about 0 wt % to about 10 wt %, preferably about 1 wt % to about 5 wt %, based on the total weight of the dispersion. Dispersants are used to "wet" the particles so that they disperse in the carrier more easily and remain dispersed over time, or to act as emulsifiers that aid in the incorporation of the dispersion in the finished formulation. Examples of dispersants include polyesters or salts of one or more hydroxycarboxylic acids, monoesters of fatty acid alkanolamides (e.g. ethanolamine, propanolamine, or aminoethyl ethanolamine), carboxylic acids and their salts based on 6-22 carbon unsaturated fatty acids, phosphate esters, neutralized phosphoric acids, stearic acids such as hydroxystearic acid, lecithin, polymers or copolymers of acrylic or methacrylic acids, ethoxy compounds (e.g. ethoxylated phosphate esters), hyperdispersants (e.g. polyhydroxy stearic acid) and TEA oleth-3 phosphate, a blend of (i) sorbitan isostearate, (ii) caprylic/capric triglyceride and (iii) di-PPG-3 myristyl ether adipate, PEG-9 polydimethylsiloxyethyl dimethicone, PEG-10 dimethicone, and polyglyceryl-6 polyricinoleate.

In one embodiment, the metal oxide is present in an amount in the weight range of about 10% to about 70% by weight, based on the total weight of the dispersion. In another embodiment, the metal oxide is present in an amount in the weight range of about 20% to about 65% by weight, based on the total weight of the dispersion. In another embodiment, the metal oxide is present in an amount in the weight range of about 40% to about 60% by weight, based on the total weight of the dispersion.

In another important embodiment of the dispersions described herein, the metal oxide particulate dispersion comprising the alkoxycrylene compound of formula (I) as the carrier is combined in a sunscreen or dermatological formulation.

A sunscreen or dermatological formulation generally includes UV-A and UV-B photoactive compounds in a cosmetically acceptable carrier, optionally including additives, such as emollients, stabilizers, emulsifiers, and combinations thereof. These additives can be used in preparing a UV filter composition in an emulsion (oil-in-water or water-in-oil) from a composition that includes one or more photoactive compounds and a solvent or a solvent combination that includes one or more organic solvents and water. When made, preferably the emulsion is an oil-in-water emulsion, wherein the oil phase is primarily formed from a mixture of an organic and/or inorganic UV filter compound(s) and one or more organic solvents.

In one embodiment, the sunscreen or dermatological formulation comprises the metal oxide particulate in an amount in the weight range of about 0.1 wt % to about 25 wt % and the alkoxycrylene compound of formula (I) in an amount in the weight range of about 0.1 wt % to about 15 wt %, based on the total weight of the formulation. In another embodiment, the sunscreen or dermatological formulation comprises the metal oxide particulate in an amount in the weight range of about 2 wt % to about 8 wt % and the alkoxycrylene compound of formula (I) in an amount in the weight range of about 1 wt % to about 7 wt %, based on the total weight of the formulation. In another embodiment, the sunscreen or dermatological formulation comprises the metal oxide particulate in an amount in the weight range of about 3 wt % to about 7 wt % and the alkoxycrylene compound of formula (I) in an amount in the weight range of about 2 wt % to about 5 wt %, based on the total weight of the formulation.

In another embodiment of the dispersions described herein, the sunscreen or dermatological formulation comprising the dispersion of the invention can further comprise additional photoactive compound(s), wherein the photoactive compound(s) act to absorb UV radiation and thereby protect the substrate (e.g., human skin, resins, films, and the like) from the harmful effects of UV radiation. The absorption process causes a photoactive compound to reach an excited state, wherein the excited state is characterized by the presence of excited electronic energy (e.g., singlet state energy or triplet state energy), as compared to the ground state of the photoactive compound. Once a photoactive compound reaches an excited state there exists a number of pathways by which the excited photoactive compound can dissipate its excess energy (e.g., singlet and/or triplet energy), however, many of those pathways adversely affect the ability of the photoactive compound to further absorb UV radiation. The alkoxycrylene molecules described herein accept electronic singlet excited state energy from UV-absorbers, particularly Avobenzone, octyl methoxycinnamate (octinoxate), and octyl salicylate (octisalate). The alkoxycrylenes also are very effective UVA absorbers in addition to providing electronic singlet state energy quenching of other UV-absorbing compounds in sunscreen compositions. The alkoxycrylene molecules described herein are especially effective when combined with one or more additional electronic singlet excited state quenching compounds such as oxybenzone. Particularly surprising photostabilization is achieved in sunscreen or dermatological formulations containing octyl methoxycinnamate and Avobenzone together with the dispersions of the invention comprising the alkoxycrylene molecules described herein.

A photoactive compound is one that responds to light photoelectrically. In the sunscreen or dermatological formulations described herein, and, in another embodiment, the dispersions described herein containing a metal oxide particulate material together with the carrier of formula (I), described in this assignee's pending application Ser. Nos. 11/891,281 and 12/022,758 filed on Aug. 9, 2007 and Jan. 30, 2008, respectively, the disclosures of which are hereby incorporated by reference, advantageously also contain a photodegradable photoactive compound. The alkoxycrylenes are useful photostabilizers and/or photoactive compounds in the dispersions described herein when combined with any single or combination of organic photoactive compounds identified in Shaath, Nadim, Encyclopedia of UV filters, © 2007, hereby incorporated by reference. Photostability is a problem with all organic UV filters because they all reach an electronic singlet excited state upon exposure to UV radiation.

It is theorized that all of the following UV filters are photostabilized by the dispersions described herein comprising inorganic particulates and the alkoxycrylene compounds of formula (I) as carriers, including each of the following, including combinations of any two or more, and include compounds selected from the following categories (with specific examples) including: p-aminobenzoic acid, its salts and its derivatives (ethyl, isobutyl, glyceryl esters; p-dimethylaminobenzoic acid); anthranilates (o-aminobenzoates; methyl, menthyl, phenyl, benzyl, phenylethyl, linalyl, terpinyl, and cyclohexenyl esters); salicylates (octyl, amyl, phenyl, benzyl, menthyl (homosalate), glyceryl, and dipropyleneglycol esters); cinnamic acid derivatives (menthyl and benzyl esters, alpha-phenyl cinnamonitrile; butyl cinnamoyl pyruvate); dihydroxycinnamic acid derivatives (umbelliferone, methylumbelliferone, methylaceto-umbelliferone); camphor derivatives (3 benzylidene, 4 methylbenzylidene, polyacrylamidomethyl benzylidene, benzalkonium methosulfate, benzylidene camphor sulfonic acid, and terephthalylidene dicamphor sulfonic acid); trihydroxycinnamic acid derivatives (esculetin, methylesculetin, daphnetin, and the glucosides, esculin and daphnin); hydrocarbons (diphenylbutadiene, stilbene); dibenzalacetone; benzalacetophenone; naphtholsulfonates (sodium salts of 2-naphthol-3,6-disulfonic and of 2-naphthol-6,8-disulfonic acids); dihydroxy-naphthoic acid and its salts; o- and p-hydroxydiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric acid derivatives; vilouric acid derivatives; tannic acid and its derivatives; hydroquinone; and benzophenones (oxybenzone, sulisobenzone, dioxybenzone, benzoresorcinol, octabenzone, 4-isopropyldibenzoyl methane, butyl methoxydibenzoyl methane, etocrylene, and 4-isopropyl-dibenzoylmethane).

The following UV filters should be particularly photostabilized by the dispersions described herein comprising inorganic particulates and the alkoxycrylene compounds of formula (I) as carriers: 2-ethylhexyl p-methoxycinnamate, 4,4'-t-butyl methoxydibenzoylmethane, octyldimethyl p-aminobenzoate, digalloyltrioleate, ethyl 4-[bis(hydroxypropyl)]aminobenzoate, 2-ethylhexylsalicylate, glycerol p-aminobenzoate, 3,3,5-trimethylcyclohexylsalicylate, and combinations thereof.

The sunscreen or dermatological formulations comprising the dispersions described herein can include a variety of photoactive compounds, preferably including one or more UV-A photoactive compounds and one or more UV-B photoactive compounds. Preferably, a sunscreen or dermatological formulation comprising the dispersion includes a photoactive compound selected from the group consisting of p-aminobenzoic acid and salts and derivatives thereof; anthranilate and derivatives thereof; dibenzoylmethane and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone naphtholsulfonate and salts and derivatives thereof; benzalacetophenone naphtholsulfonate and salts and derivatives thereof; dihydroxy-naphthoic acid and salts thereof; o-hydroxydiphenyldisulfonate and salts and derivatives thereof; p-hydroxydiphenyldisulfonate and salts and derivatives thereof; coumarin and derivatives thereof; diazole derivatives; quinine derivatives and salts thereof; quinoline derivatives; uric acid derivatives; vilouric acid derivatives; tannic acid and derivatives thereof; hydroquinone; diethylamino hydroxybenzoyl hexyl benzoate and salts and derivatives thereof; and combinations of the foregoing.

In a particular embodiment, the sunscreen or dermatological formulations comprising the dispersions described herein further include a dibenzoylmethane derivative, such as PARSOL 1789 (Avobenzone).

UV A radiation (about 320 nm to about 400 nm), is recognized as contributing to causing damage to skin, particularly to very lightly colored or sensitive skin. A sunscreen or dermatological formulation comprising the dispersion of the invention disclosed herein preferably includes a UV-A photoactive compound. Preferably, a sunscreen or dermatological formulation comprising the dispersion of the invention disclosed herein includes a dibenzoylmethane derivative UV-A photoactive compound. Preferred dibenzoylmethane derivatives include, 2-methyldibenzoylmethane; 4-methyldibenzoylmethane; 4-isopropyldibenzoylmethane; 4-tert-butyldibenzoylmethane; 2,4-dimethyldibenzoylmethane; 2,5-dimethyldibenzoylmethane; 4,4'-diisopropyldibenzoylmethane; 4,4'-dimethoxydibenzoylmethane; 4-tert-butyl-4'-methoxydibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; 2,6-dimethyl-4-tert-butyl-4'-methoxydibenzoylmethane, and combinations thereof.

For a product marketed in the United States, preferred cosmetically acceptable photoactive compounds and concentrations (reported as a percentage by weight of the total cosmetic sunscreen composition) include: aminobenzoic acid (also called para aminobenzoic acid and PABA; 15% or less), Avobenzone (also called butyl methoxy dibenzoylmethane; 3% or less), cinoxate (also called 2 ethoxyethyl p methoxycinnamate; 3% or less), dioxybenzone (also called benzophenone 8; 3% or less), homosalate ((also called 3,3,5-trimethylcyclohexyl salicylate, 15% or less), menthyl anthranilate (also called menthyl 2 aminobenzoate; 5% or less), octocrylene (also called 2 ethylhexyl 2 cyano 3,3 diphenylacrylate; 10% or less), octyl methoxycinnamate (7.5% or less), octyl salicylate (also called 2 ethylhexyl salicylate; 5% or less), oxybenzone (also called benzophenone 3; 6% or less), padimate 0 (also called octyl dimethyl PABA; 8% or less), phenylbenzimidazole sulfonic acid (water soluble; 4% or less), sulisobenzone (also called benzophenone 4; 10% or less), titanium dioxide (25% or less), trolamine salicylate (also called triethanolamine salicylate; 12% or less), and zinc oxide (25% or less).

Other preferred cosmetically acceptable photoactive compounds and preferred concentrations (percent by weight of the total cosmetic sunscreen composition) include diethanolamine methoxycinnamate (10% or less), ethyl-[bis(hydroxypropyl)] aminobenzoate (5% or less), glyceryl aminobenzoate (3% or less), 4 isopropyl dibenzoylmethane (5% or less), 4 methylbenzylidene camphor (6% or less), terephthalylidene dicamphor sulfonic acid (10% or less), and sulisobenzone (also called benzophenone 4, 10% or less).

For a product marketed in the European Union, preferred cosmetically acceptable photoactive compounds and preferred concentrations (reported as a percentage by weight of the total cosmetic sunscreen composition) include: PABA (5% or less), camphor benzalkonium methosulfate (6% or less), homosalate (10% or less), benzophenone 3 (10% or less), phenylbenzimidazole sulfonic acid (8% or less, expressed as acid), terephthalidene dicamphor sulfonic acid (10% or less, expressed as acid), butyl methoxydibenzoylmethane (5% or less), benzylidene camphor sulfonic acid (6% or less, expressed as acid), octocrylene (10% or less, expressed as acid), polyacrylamidomethyl benzylidene camphor (6% or less), ethylhexyl methoxycinnamate (10% or less), PEG 25 PABA (10% or less), isoamyl p methoxycinnamate (10% or less), ethylhexyl triazone (5% or less), drometrizole trielloxane (15% or less), diethylhexyl butamido triazone (10% or less), 4 methylbenzylidene camphor (4% or less), 3 benzylidene camphor (2% or less), ethylhexyl salicylate (5% or less), ethylhexyl dimethyl PABA (8% or less), benzophenone 4 (5%, expressed as acid), methylene bis benztriazolyl tetramethylbutylphenol (10% or less), disodium phenyl dibenzimidazole tetrasulfonate (10% or less, expressed as acid), bis ethylhexyloxyphenol methoxyphenol triazine (10% or less), methylene bisbenzotriazolyl tetramethylbutylphenol (10% or less, also called TINOSORB M or Bisoctrizole), and bisethylhexyloxyphenol methoxyphenyl triazine (10% or less, also called TINOSORB S or Bemotrizinol).

All of the above described UV filters are commercially available. For example, suitable commercially available organic UV filters are identified by trade name and supplier in Table 2 below:

TABLE 2

| CTFA Name | Trade Name | Supplier |
|---|---|---|
| benzophenone-3 | UVINUL M-40 | BASF Chemical Co. |
| benzophenone-4 | UVINUL MS-40 | BASF Chemical Co. |
| benzophenone-8 | SPECTRA-SORB UV-24 | American Cyanamid |
| DEA-methoxycinnamate | BERNEL HYDRO | Bernel Chemical |
| diethylamino hydroxybenzoyl hexyl benzoate | UVINUL A-PLUS | BASF Chemical Co. |
| diethylhexyl butamido triazone | UVISORB HEB | 3V-Sigma |
| disodium phenyl dibenzylimidazole | NEO HELIOPAN AP | Symrise |
| ethyl dihydroxypropyl-PABA | AMERSCREEN P | Amerchol Corp. |
| glyceryl PABA | NIPA G.M.P.A. | Nipa Labs. |
| homosalate | KEMESTER HMS | Humko Chemical |
| menthyl anthranilate | SUNAROME UVA | Felton Worldwide |
| octocrylene | UVINUL N-539 | BASF Chemical Co. |
| octyl dimethyl PABA | AMERSCOL | Amerchol Corp. |
| octyl methoxycinnamate | PARSOL MCX | Bernel Chemical |
| PABA | PABA | National Starch |
| 2-phenylbenzimidazole-5-sulphonic acid | EUSOLEX 6300 | EM Industries |
| TEA salicylate | SUNAROME W | Felton Worldwide |
| 2-(4-methylbenzildene)-camphor | EUSOLEX 6300 | EM Industries |
| benzophenone-1 | UVINUL 400 | BASF Chemical Co. |
| benzophenone-2 | UVINUL D-50 | BASF Chemical Co. |
| benzophenone-6 | UVINUL D-49 | BASF Chemical Co. |
| benzophenone-12 | UVINUL 408 | BASF Chemical Co. |
| 4-isopropyl dibenzoyl methane | EUSOLEX 8020 | EM Industries |
| butyl methoxy dibenzoyl methane | PARSOL 1789 | Givaudan Corp. |
| etocrylene | UVINUL N-35 | BASF Chemical Co. |
| methylene bisbenzotriazolyl tetramethylbutylphenol | TINOSORB M | Ciba Specialty Chemicals |
| bisethylhexyloxyphenol methoxyphenyl triazine. | TINOSORB S | Ciba Specialty Chemicals |

Commonly-assigned U.S. Pat. Nos. 6,485,713 and 6,537,529, the disclosures of which are hereby incorporated herein by reference, describe compositions and methods for increasing the photostability of photoactive compounds in a sunscreen or dermatological formulation, e.g., by the addition of polar solvents to the oil phase of a formulation. By increasing the polarity of the oil phase of a sunscreen or dermatological formulation that includes an alkoxycrylene, e.g., methoxycrylene, as carrier, and a particulate material as described herein, the stability of the sunscreen or dermatological formulation is surprisingly increased in comparison to other carriers. In the sunscreen or dermatological formulations described herein, therefore, preferably, one or more of a highly polar solvent is present in the oil-phase of the formulation. Preferably, a sufficient amount of a polar solvent is present in the sunscreen or dermatological compositions described herein to raise the dielectric constant of the oil-phase of the composition to a dielectric constant of at least about 7, preferably at least about 8. With or without the highly polar solvent in the oil phase, the alkoxycrylene molecules described herein yield unexpected photostability in comparison to other carriers.

A photoactive compound can be considered stable when, for example, after 30 MED irradiation the photoactive compound has retained at least about 90% of its original absorbance at a wavelength, or over a range of wavelengths of interest (e.g., the wavelength at which a photoactive compound has a peak absorbance, such as 350-370 nm for Avobenzone). Likewise, a sunscreen or dermatological formulation comprising the dispersion of the invention can include a plurality of photoactive compounds and a sunscreen or dermatological formulation comprising the dispersion of the invention, as a whole, can be considered stable when, for example, after 30 MED irradiation the sunscreen composition has retained at least about 90% of its original absorbance at one or more wavelengths of interest (e.g., at or near the peak absorbance wavelength of the primary photoactive compound).

In accordance with another embodiment of the invention, the sunscreen or dermatological formulations, including the dispersions described herein, also include a dibenzoylmethane derivative, such as PARSOL 1789 (Avobenzene) and/or a dialkyl naphthalate ester.

Commonly-assigned U.S. Pat. No. 5,993,789, which is hereby incorporated herein by reference, describes the use of diesters and/or polyesters of a naphthalene dicarboxylic acid (dialkyl naphthalate esters) as being surprisingly effective in photostabilizing dibenzoylmethane derivatives, particularly PARSOL 1789 (Avobenzone).

In accordance with yet another embodiment, dialkyl naphthalate esters for which $R^1$ and/or $R^2$ represent branched alkyl groups with 6 to 10 carbon atoms are advantageous, as described in U.S. Pat. Nos. 5,993,789 and 6,113,931, the disclosures of which are hereby incorporated by reference. Diethylhexyl naphthalate esters, as described in U.S. Pat. Nos. 5,993,789 and 6,113,931, are very particularly preferred which are available, e.g., under the trade name Hallbrite TQ™ from CP Hall or Corapan TQ™ from H&R.

According to this dialkyl naphthalate ester embodiment, the sunscreen or dermatological formulations described herein may advantageously contain from about 0.001% to about 30% by weight, preferably from about 0.01% to about 20% by weight, very particularly preferred from about 0.5% to about 15% by weight, of one or more dialkyl naphthalate esters, as described in U.S. Pat. Nos. 5,993,789 and 6,113,931.

In accordance with another important embodiment, a sunscreen or dermatological formulation comprising a particulate material/formula (I) dispersion is combined with a water soluble UV filter compound and/or a broad-band filter compound and optionally, but preferably, together with a dibenzoylmethane derivative and/or a dialkyl naphthalate ester.

Water-soluble UV filter substances that are advantageously included in the dispersions described herein, in another embodiment, are sulfonated UV filters, in particular: phenylene-1,4-bis(2-benzimidazyl)-3,3'-5,5'-tetrasulfonic acid, which has the following structure:

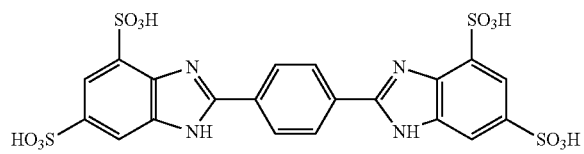

and its salts, especially the corresponding sodium, potassium or triethanolammonium salts, in particular phenylene-1,4-bis(2-benzimidazyl)-3,3'-5,5'-tetrasulfonic acid bissodium salt

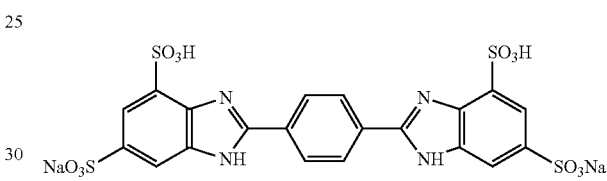

with the INCI name disodium phenyl dibenzimidazole tetrasulfonate (CAS No.: 180898-37-7), which is obtainable for example under the proprietary name Neo Heliopan A P from Haarmann & Reimer.

Further advantageous sulfonated UV filters are the salts of 2-phenylbenzimidazole-5-sulfonic acid, such as its sodium, potassium or its triethanolammonium salts, and the sulfonic acid itself

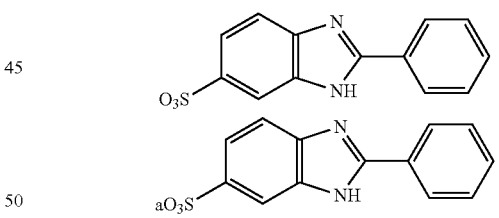

with the INCI name phenylbenzimidazole sulfonic acid (CAS No. 27503-81-7), which is obtainable for example under the proprietary name Eusolex 232 from Merck or under Neo Heliopan Hydro from Haarmann & Reimer.

Further advantageous water-soluble UV-B and/or broad-band filter substances for the purposes of this water-soluble UV filter-containing embodiment are, for example, sulfonic acid derivatives of 3-benzylidenecamphor, such as, for example, 4-(2-oxo-3-bornylidenemethyl)benzene-sulfonic acid, 2-methyl-5-(2-oxo-3-bornylidenemethyl)sulfonic acid and the salts thereof.

The total amount of one or more water-soluble UV filter substances in the sunscreen or dermatological formulations of this embodiment is advantageously chosen from the range of about 0.01% by weight to about 20% by weight, preferably from about 0.1 to about 10% by weight, in each case based on the total weight of the formulations.

In accordance with another important embodiment, the sunscreen or dermatological formulation comprising dispersion is combined with a hydroxybenzophenone compound and/or a broad-band filter compound and optionally, but preferably, together with a dibenzoylmethane derivative and/or a dialkyl naphthalate ester.

Hydroxybenzophenones are characterized by the following structural formula:

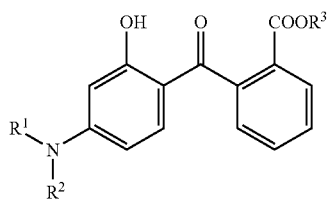

where $R^1$ and $R^2$ independent of one another are hydrogen, $C_1$-$C_{20}$-alkyl, $C_3$-$C_{10}$-cycloalkyl or $C_3$-$C_{10}$-cyloalkenyl, wherein the substituents $R^1$ and $R^2$ together with the nitrogen atom to which they are bound can form a 5- or 6-ring and $R^3$ is a $C_1$-$C_{20}$ alkyl radical.

A particularly advantageous hydroxybenzophenone is the 2-(4'-diethylamino-2'-hydroxybenzoyl)benzoic acid hexyl ester (also: aminobenzophenone) which is characterized by the following structure:

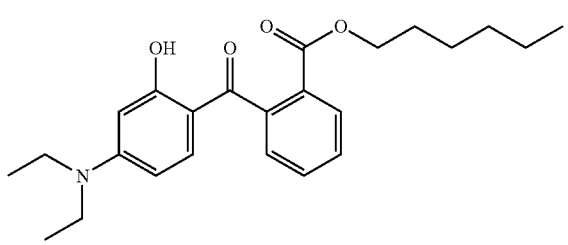

and is available from BASF under the Uvinul A Plus.

According to this hydroxybenzophenone-containing embodiment, sunscreen or dermatological formulations described herein contain from about 0.1% to about 20% by weight, advantageously from about 0.1% to about 15% by weight, very particularly preferred from about 0.1% to about 10% by weight, of one or more hydroxybenzophenones.

In accordance with another important embodiment, a sunscreen or dermatological formulation containing the particulate material/formula (I) dispersion is combined with a benzotriazole derivative compound and/or a broad-band filter compound and optionally, but preferably, together with a dibenzoylmethane derivative and/or a dialkyl naphthalate ester.

One disadvantage of combining benzotriazole compounds with the dispersions described herein is the characteristic of forming imperceptibly thin films on the skin which have unpleasant tactile properties. Another disadvantage is that such benzotriazole derivatives show only inadequate solubility, if any, in conventional oil components. Well-known solvents can dissolve only up to a maximum of about 15% by weight of these compounds, which usually corresponds to a concentration of about 1% to about 1.5% by weight of dissolved (=active) filter substance in the complete cosmetic or dermatological preparation. Consequently, only comparatively low sun protection factors have been achievable with these filter substances because their solubility or dispersibility in the formulations is too low, i.e. they can be satisfactorily incorporated into such formulations only with difficulty or not at all.

Even if it is also possible in principle to achieve a certain UV protection when the solubility is limited, another problem frequently occurs, that is recrystallization. Substances of low solubility in particular recrystallize comparatively rapidly, which may be induced by fluctuations in temperature or other influences. Uncontrolled recrystallization of an essential ingredient of a preparation such as a UV filter has, however, extremely disadvantageous effects on the properties of the given preparation and, not least, on the desired light protection.

It was also surprising and not predictable for the skilled worker that the disadvantages of the prior art, with respect to the benzotriazole-containing embodiment of the dispersions described herein, are remedied by active ingredient combinations effective for light protection and composed of (a) one or more UV filter substances selected from the group of benzotriazole derivatives;

(b) an alkoxycrylene of formula (I); and optionally (c) one or more dialkyl naphthalate esters having the structural formula:

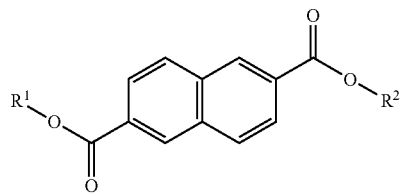

described in U.S. Pat. Nos. 5,993,789 and 6,113,931. in which $R^1$ and $R^2$ are, independently of one another, selected from the group of branched and unbranched alkyl groups having 6 to 24 carbon atoms.

In accordance with yet another benzotriazole-containing embodiment of the dispersions described herein, the dispersions include a benzotriazole compound having a structural formula:

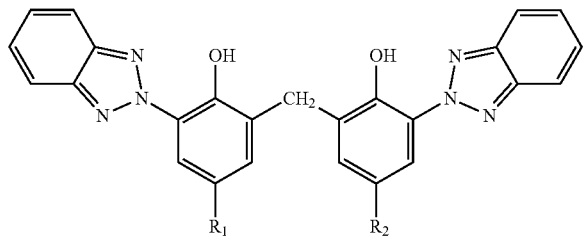

where $R_1$ and $R_2$ are, independently of one another, selected from the group of branched or unbranched $C_1$-$C_{18}$-alkyl radicals, of $C_5$-$C_{12}$-cycloalkyl or aryl radicals which are optionally substituted by one or more $C_1$-$C_4$ alkyl groups.

The preferred benzotriazole derivative is 2,2'-methylenebis(6-(2H-benzotriazol-2-yl)-4-(1,1,3,3-tetramethylbutyl)phenol), obtainable under the proprietary name Tinosorb® from CIBA-Chemikalien GmbH (INCI: bisoctyltriazole), which is characterized by the chemical structural formula:

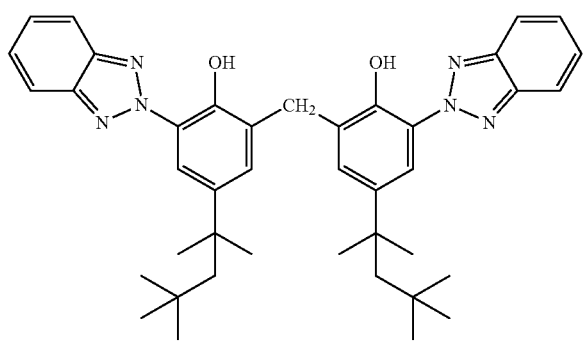

and is distinguished by good UV absorption properties.

Another advantageous broadband filter that can be combined with the dispersion in this benzotriol-containing embodiment is 2-(2H-benzotriazol-2-yl)-4-methyl-6-[2-methyl-3-[1,3,3,3-tetramethyl-1-[(trimethyl-silyl)oxy]disiloxa-nyl]propyl]phenol (CAS No.: 155633-54-8) with the INCI name drometrizole trisiloxane, which is characterized by the chemical structural formula

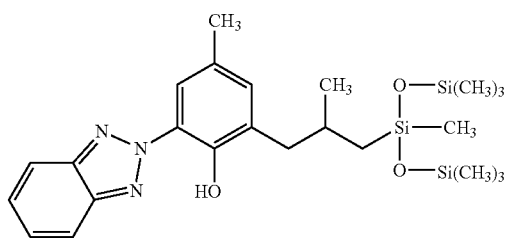

The total amount of one or more benzotriazole derivatives, in particular of 2,2'-methylenebis(6-(2H-benzotriazol-2-yl)-4-(1,1,3,3-tetramethylbutyl)phenol) and/or 2-(2H-benzotria-zol-2-yl)-4-methyl-6-[2-methyl-3-[1,3,3,3-tetramethyl-1-[(trimethylsilyl)oxy]disiloxa-nyl]propyl]phenol, in the finished cosmetic or dermatological composition is advantageously in the range from about 0.1% to about 15.0% by weight, preferably from about 0.5% to about 10.0% by weight, based on the total weight of the compositions.

In accordance with another important embodiment, the sunscreen or dermatological formulation containing the particulate material/formula (I) dispersion is combined with an asymmetrically substituted triazine derivative and/or a broadband filter compound and optionally, but preferably, together with a dibenzoylmethane derivative and/or a dialkyl naphthalate ester to obtain an increased sun protection factor.

Asymmetrically substituted triazine derivatives display a good light protection effect. Their main disadvantage is, however, that their solubility is low in conventional oil components. Well-known solvents can dissolve only up to a maximum of about 15% by weight of these compounds, which usually corresponds to a concentration of about 1% to about 1.5% by weight of dissolved (=active) filter substance in the complete sunscreen or dermatological formulation.

One disadvantage of the prior art with respect to asymmetrically substituted triazine derivatives is accordingly that generally only comparatively low sun protection factors have been achievable with these filter substances because their solubility or dispersibility in the formulations is too low, i.e. they can be satisfactorily incorporated into such formulations only with difficulty or not at all.

Even if it is also possible in principle to achieve a certain UV protection when the solubility is limited, another problem frequently occurs, that is recrystallization. Substances of low solubility in particular recrystallize comparatively rapidly, which may be induced by fluctuations in temperature or other influences. Uncontrolled recrystallization of an essential ingredient of a preparation such as a UV filter has, however, extremely disadvantageous effects on the properties of the given preparation and, not least, on the desired light protection.

Disadvantages of the prior art with respect to asymmetrically substituted triazine derivatives are remedied by active ingredient combinations effective for light protection and composed of:

(a) one or more UV filter substances selected from the group of asymmetrically substituted triazine derivatives, and (b) one or more alkoxycrylenes having the structural formula (I); and (c) optionally a dibenzoylmethane derivative and/or a dialkyl naphthalate ester.

Advantageous asymmetrically substituted s-triazine derivatives within the meaning of this embodiment are, for example, those described in EP-A-570 838, whose chemical structure is represented by the generic formula

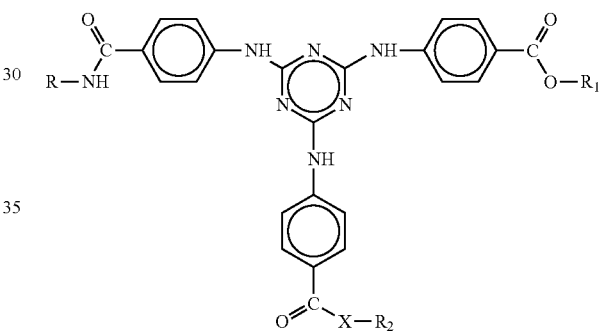

where
R is a branched or unbranched $C_1$-$C_{18}$-alkyl radical, a $C_5$-$C_{12}$-cycloalkyl radical, optionally substituted by one or more $C_1$-$C_4$-alkyl groups, and
X is an oxygen atom or an NH group,
$R_1$ is a branched or unbranched $C_1$-$C_{18}$-alkyl radical, a $C_5$-$C_{12}$-cycloalkyl radical, optionally substituted by one or more $C_1$-$C_4$-alkyl groups, or a hydrogen atom, an alkali metal atom, an ammonium group or a group of the formula

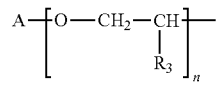

in which
A is a branched or unbranched $C_1$-$C_{18}$-alkyl radical, a $C_5$-$C_{12}$-cycloalkyl or aryl radical, optionally substituted by one or more $C_1$-$C_4$-alkyl groups,
$R_3$ is a hydrogen atom or a methyl group,
n is a number from 1 to 10,
$R_2$ is a branched or unbranched $C_1$-$C_{18}$-alkyl radical, a $C_5$-$C_{12}$-cycloalkyl radical, optionally substituted by one or more $C_1$-$C_4$-alkyl groups, and
if X is the NH group, $R_2$ is a branched or unbranched $C_1$-$C_{18}$-alkyl radical, a $C_5$-$C_{12}$-cycloalkyl radical, optionally substituted by one or more $C_1$-$C_4$-alkyl groups, or a hydrogen atom, an alkali metal atom, an ammonium group or a group of the formula

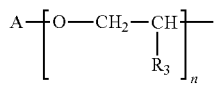

in which

A is a branched or unbranched $C_1$-$C_{18}$-alkyl radical, a $C_5$-$C_{12}$-cycloalkyl or aryl radical, optionally substituted by one or more $C_1$-$C_4$-alkyl groups, $R_3$ is a hydrogen atom or a methyl group, n is a number from 1 to 10, if X is an oxygen atom.

In a preferred form of this triazine-containing embodiment, the sunscreen or dermatological formulations comprising the dispersions described herein include a content of least one asymmetrically substituted s-triazine selected from the group of bisresorcinyltriazine substances having the following structural formula:

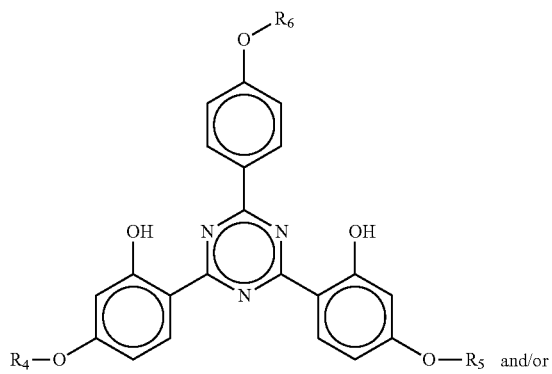 and/or

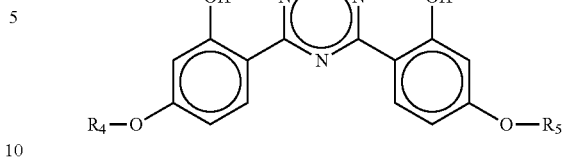

All of the bisresorcinyltriazines are advantageous for this embodiment. Particularly advantageous bisresorcinyltriazines comprise $R_4$ and $R_5$ selected from the group of branched or unbranched alkyl groups of 1 to 18 carbon atoms. The alkyl groups may also again advantageously be substituted by silyloxy groups. $A_1$ is advantageously a substituted homocyclic or heterocyclic aromatic five-membered ring or six-membered ring.

The following compounds are very particularly advantageous:

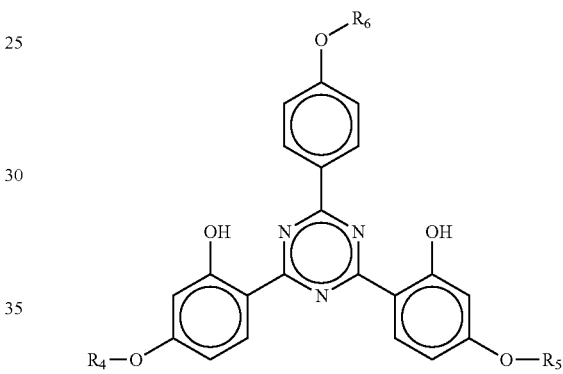

where $R_6$ is a hydrogen atom or a branched or unbranched alkyl group with 1 to 10 carbon atoms, in particular 2,4-bis{[4-(2-ethylhexyloxy)-2-hydroxy]phenyl}-6-(4-methoxyphenyl)-1,3,5-triazine (INCI: aniso triazine), which is obtainable under the proprietary name Tinosorb® S from CIBA-Chemikalien GmbH and is characterized by the following structure:

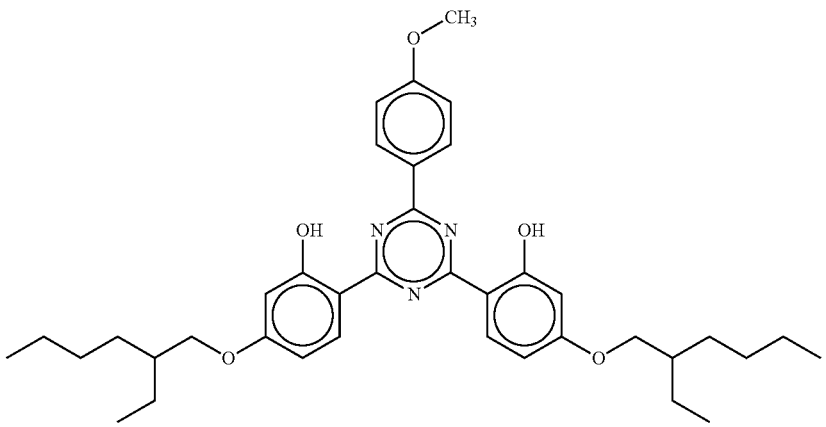

Also advantageous is 2,4-bis{[4-(3-sulfonato-2-hydroxypropyloxy)-2-hydroxy]phenyl}-6-(4-methoxy phenyl)-1,3,5-triazine sodium salt, which is characterized by the following structure:

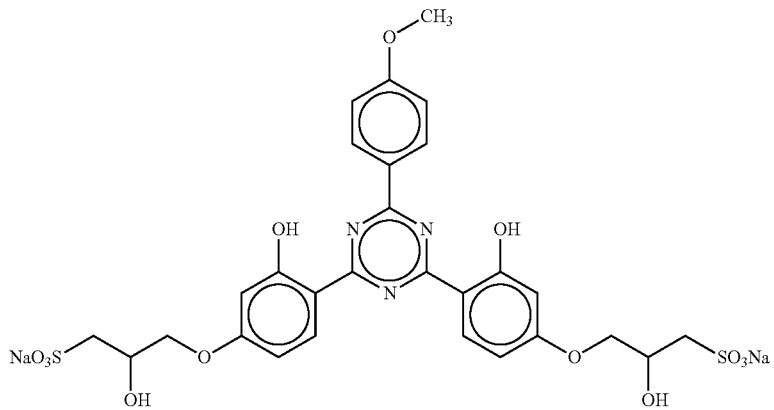

Also advantageous is 2,4-bis{[4-(3-(2-propyloxy)-2-hydroxypropyloxy)-2-hydroxy]phenyl}-6(4-meth oxyphenyl)-1,3,5-triazine, which is characterized by the following structure:

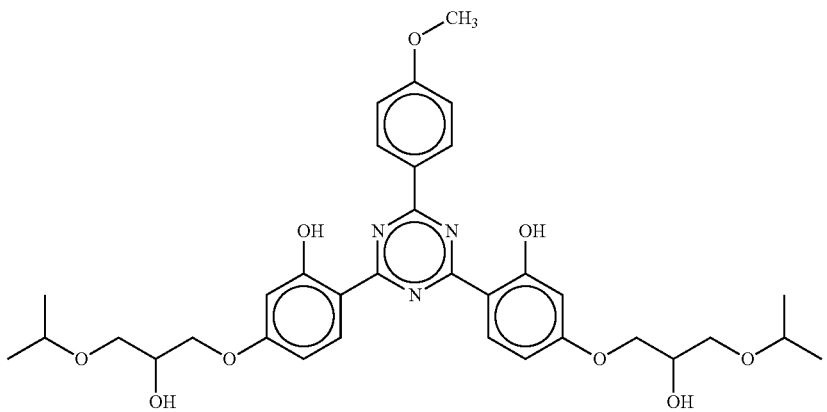

Also advantageous is 2,4-bis{[4-(2-ethylhexyloxy)-2-hydroxy]phenyl}-6-[4-(2-methoxyethoxycarbonyl)phenylamino]-1,3,5-triazine, which is characterized by the following structure:

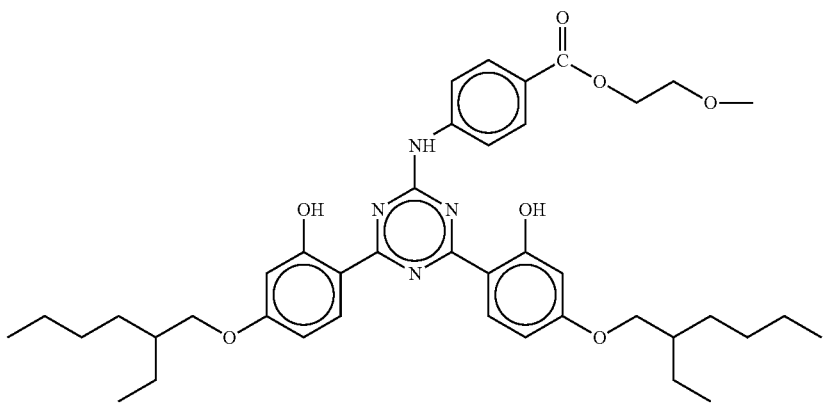

Also advantageous is 2,4-bis{[4-(3-(2-propyloxy)-2-hydroxypropyloxy)-2-hydroxy]phenyl}-6-[4-(ethoxycarbonyl) phenylamino]-1,3,5-triazine which is characterized by the following structure:

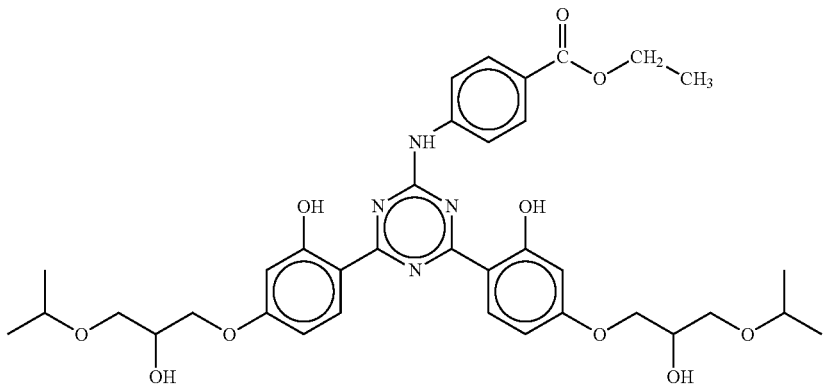

Also advantageous is 2,4-bis{[4-(2-ethylhexyloxy)-2-hydroxy]phenyl}-6-(1-methylpyrrol-2-yl)1,3,5-triazine, which is characterized by the following structure:

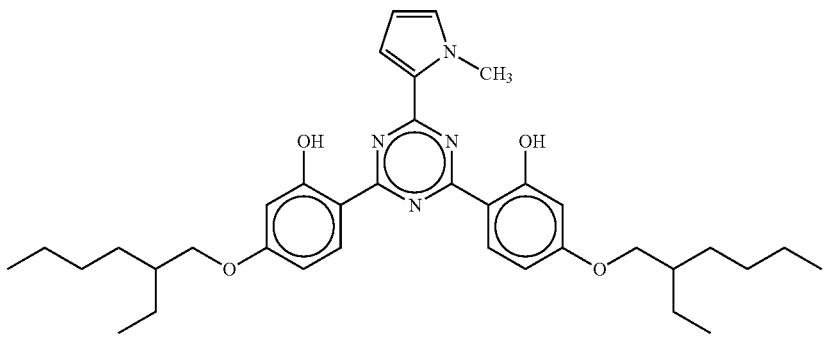

Also advantageous is 2,4-bis{[4-tris(trimethylsiloxysilyl-propyloxy)-2-hydroxy]phenyl}-6-(4-meth oxyphenyl)-1,3,5-triazine, which is characterized by the following structure:

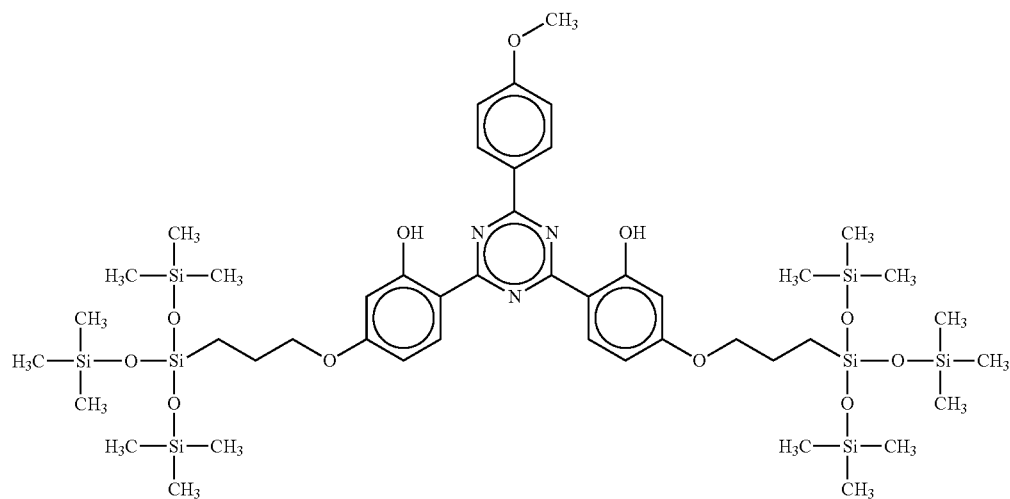

Also advantageous is 2,4-bis{[4-(2-methylpropenyloxy)-2-hydroxy]phenyl}-6-(4-methoxyphenyl)-1,3,5-triazine, which is characterized by the following structure:

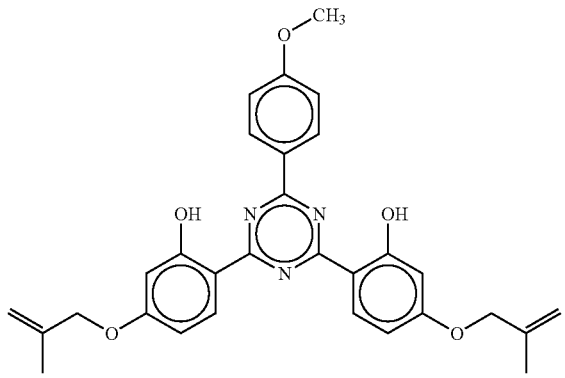

Also advantageous is 2,4-bis{[4-(1',1',1',3',5',5',5'-heptamethylsiloxy-2-methylpropyloxy)-2-hydroxy]-phenyl}-6-(4-methoxyphenyl)-1,3,5-triazine, which is characterized by the following structure:

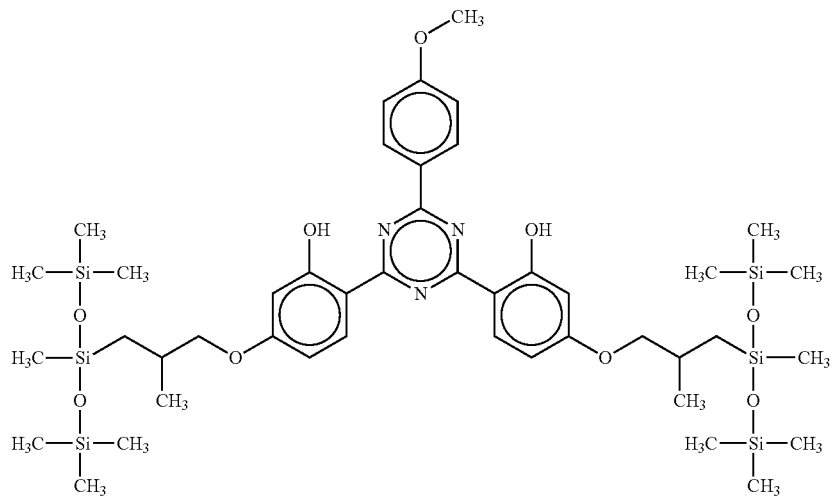

In another embodiment, the sunscreen or dermatological formulations comprising the dispersions described herein include an asymmetrically substituted s-triazine whose chemical structure is represented by the formula

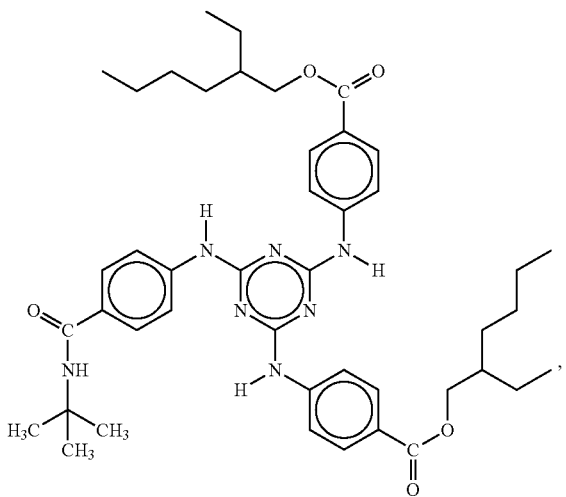

which is also referred to hereinafter as dioctylbutylamidotriazone (INCI) and is obtainable under the proprietary name UVASORB HEB from Sigma 3 V.

The asymmetrically substituted s-triazine derivative(s) of the invention are advantageously, but optionally, incorporated into the oil phase of the sunscreen or dermatological formulation comprising the particulate material/formula (I) dispersions described herein.

The total amount of one or more asymmetrically substituted s-triazine derivatives, in particular of dioctylbutylamidotriazone, in the sunscreen or dermatological formulation comprising the particulate material/formula (I) dispersions described herein is advantageously chosen from the range from about 0.1% to about 15.0% by weight, preferably from about 0.5% to about 10.0% by weight, based on the total weight of the formulation.

The sunscreen or dermatological formulations comprising the particulate material/formula (I) dispersions described herein can be used for cosmetic or dermatological UV light-protection, and/or for the treatment, care and cleansing of the skin and/or hair and as a cosmetic product in decorative cosmetics. These compositions, with or without additional UV filter(s) and/or dispersing aids, and/or other additives are applied to the skin and/or the hair in a sufficient quantity in the manner customary for cosmetics.

The sunscreen or dermatological formulations comprising the particulate material/formula (I) dispersions described herein can comprise cosmetic auxiliaries such as those conventionally used in such formulations, e.g. preservatives, bactericides, perfumes, antifoams, dyes, pigments which have a coloring effect, thickeners, moisturizers and/or humectants, fats, oils, waxes or other conventional constituents of a sunscreen or dermatological formulation, such as alcohols, polyols, polymers, foam stabilizers, electrolytes, organic solvents or silicone derivatives.

In accordance with another embodiment, one or more antioxidants may be added to the particulate material/formula (I) dispersions described herein. According to this embodiment, any antioxidant suitable or conventional for sunscreen or dermatological applications can be used.

Particularly advantageous antioxidants are chosen from the group consisting of amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. alpha.-carotene, .beta.-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, .gamma.-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocysteine sulfoximine, buthionine sulfones, penta-, hexa-, heptathionine sulfoximine) in very low tolerated doses (e.g. pmol to ·mu·mol/kg), and also (metal) chelating agents (e.g. .alpha.-hydroxy fatty acids, palmitic acid, phytic acid, lactoferrin), .alpha.-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. .gamma.-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of gum benzoin, rutinic acid and derivatives thereof, .alpha.-glycosylrutin, ferulic acid, furfurylideneglucitol, carnosine, butylhydroxytoluene, butylhydroxyanisole, nordihydroguaiaretic acid, trihydroxybutyro-phenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of said active ingredients which are suitable according to the invention.

The amount of antioxidants (one or more compounds) in the formulations is preferably from about 0.001% to about 30% by weight, particularly preferably from about 0.05% to about 20% by weight, in particular from about 0.1% to about 10% by weight, based on the total weight of the preparation.

If vitamin E and/or derivatives thereof are the antioxidant or antioxidants, it is advantageous to choose their respective concentrations from the range from about 0.001% to about 10% by weight, based on the total weight of the formulation.

If vitamin A, vitamin A derivatives, carotenes, or carotene derivatives are the antioxidant or antioxidants, it is advantageous to choose their respective concentrations from the range from about 0.001% to about 10% by weight, based on the total weight of the formulation.

It is particularly advantageous when the sunscreen or dermatological formulations comprising the comprising the particulate material/formula (I) dispersions described herein comprise further cosmetic or dermatological active ingredients, preferred active ingredients being antioxidants which can protect the skin against oxidative stress.

Advantageous further active ingredients are natural active ingredients and/or derivatives thereof, such as e.g. ubiquinones, retinoids, carotenoids, creatine, taurine and/or β-alanine.

Sunscreen or dermatological formulations comprising the particulate material/formula (I) dispersions described herein, which comprise e.g. known antiwrinkle active ingredients, such as flavone glycosides (in particular α-glycosylrutin), coenzyme Q10, vitamin E and/or derivatives and the like, are particularly advantageously suitable for the prophylaxis and treatment of cosmetic or dermatological changes in skin, as arise, for example, during skin aging (such as, for example, dryness, roughness and formation of dryness wrinkles, itching, reduced refatting (e.g. after washing), visible vascular dilations (teleangiectases, couperosis), flaccidity and formation of wrinkles and lines, local hyperpigmentation, hypopigmentation and abnormal pigmentation (e.g. age spots), increased susceptibility to mechanical stress (e.g. cracking) and the like). In addition, they are advantageously suitable against the appearance of dry or rough skin.

In accordance with another important embodiment, the sunscreen or dermatological formulation comprising the particulate material/formula (I) dispersions described herein may be combined with one or more hydrophilic skincare active ingredients and/or broad-band filter compounds and optionally, but preferably, together with a dibenzoylmethane derivative.

Advantageous hydrophilic active ingredients which (individually or in any combinations with one another) are stabilized by their use together with the dispersions described herein include those listed below:

biotin; carnitine and derivatives; creatine and derivatives; folic acid; pyridoxine; niacinamide; polyphenols (in particular flavonoids, very particularly alpha-glucosylrutin) ascorbic acid and derivatives; Hamamelis; Aloe Vera; panthenol; amino acids.

Particularly advantageous hydrophilic active ingredients for the purposes of this embodiment are also water-soluble antioxidants, such as, for example, vitamins.

The amount of hydrophilic active ingredients (one or more compounds) in the formulations is preferably from about 0.0001% to about 10% by weight, particularly preferably from about 0.001% to about 5% by weight, based on the total weight of the formulation.

In accordance with one important embodiment, the sunscreen or dermatological formulation comprising the particulate material/formula (I) dispersions described herein are combined with a lipophilic oxidation or UV-sensitive active ingredients, such as retinoic acid and its derivatives, e.g., tretinoin or isotretinoin and/or a broad-band filter compound and optionally, but preferably, together with a dibenzoylmethane derivative.

Advantageous lipophilic active ingredients which are stabilized in an excellent manner with the formula (I)-containing dispersions described herein are those whose log P value is greater than 3.5. P is the partition coefficient, which is defined as the ratio of the equilibrium concentration of a dissolved substance in a two-phase system which consists of two solvents which are essentially immiscible with one another. These two solvents are, in the present case, n-octanol and water, i.e.

$$P_{ow} = \frac{C_{n-octanol}}{C_{water}}.$$

It is advantageous for the purposes of this embodiment to choose the lipophilic active ingredients from the group of ubiquinones and plastoquinones. For the purposes of this embodiment of the present invention, coenzyme Q10, which has a log P value of about 15, is very particularly advantageous.

It was particularly surprising that very advantageous preparations according to this embodiment can be obtained when the lipophilic active ingredient(s) combined with the particulate material/formula (I) components of the dispersion is/are chosen from the group of ubiquinones.

Further lipophilic active ingredients which are advantageous according to this embodiment are retinoid compounds (vitamin A acid and/or derivatives thereof). The group of retinoids advantageous according to this embodiment of the invention is defined as including all cosmetically and/or pharmaceutically acceptable retinoids, including retinol and its esters, retinal and also retinoic acid (vitamin A acid) and esters thereof. For the purposes of this embodiment of the present invention, retinol (with a log P value of about 7) and retinyl palmitate (with a log P value of about 13) are particularly advantageous.

Further lipophilic acid ingredients advantageous according to this embodiment are carotenoids. For the purposes of this embodiment, β-carotene, which has a log P value of 15, for example, is particularly advantageous.

Further advantageous lipophilic active ingredients are: lipoic acid and derivatives, vitamin E and derivatives, vitamin F, dioic acid [8-hexadecene-1,16-dicarboxylic acid (CAS number 20701-68-2)]

The amount of lipophilic active ingredients (one or more compounds) in the sunscreen or dermatological formulations described herein is preferably from about 0.0001% to about 10% by weight, particularly preferably from about 0.001% to about 5% by weight, based on the total weight of the formulation.

EXAMPLES

Example 1

Formulations of Zinc Oxide with a Formula (I) Carrier

Zinc oxide dispersions using ethylhexyl methoxycrylene (SOLASTAY™ $S_1$), butyloctyl salicylate (control), or C12-15 alkyl benzoate (control) as carriers were supplied by either Dynamic Dispersions LLC "DCI" or Kobo Products "Kobo" and formulated as shown in Table 3. The zinc oxide particles (Z-Cote HP1) comprise a 2% dimethicone coating and were supplied by BASF.

Sunscreens were formulated comprising 10% to 13.3% of the zinc oxide dispersions of Table 3 and the SPF and UVA-PF values were determined as shown in Table 4. Control sunscreen formulations comprising dispersions of zinc oxide and either butyloctyl salicylate or C12-C15 alkyl benzoates as the carrier had low SPF and UVA-PF values. Control sunscreen formulations comprising ethylhexyl methoxycrylene (SOLASTAY™ $S_1$) and no zinc oxide also had low SPF and UVA-PF values. However, sunscreen formulations comprising dispersions of zinc oxide with ethylhexyl methoxycrylene (SOLASTAY™ $S_1$) as the carrier had significantly higher SPF and UVA-PF values. The exact compositions of the zinc oxide sunscreen formulations of Table 4 are shown in Table 5.

TABLE 3

Dispersions of Zinc Oxide Using a Formula (I) Carrier

| Ingredients | D-1 | D-2 | D-3 | D-4 |
|---|---|---|---|---|
| Zinc Oxide (Z-Cote HP1) | 60-64% | 62% | 46.59% | 47.00-51.00% |
| Ethylhexyl methoxycrylene (SOLASTAY ™ $S_1$) | | 34% | | 23.00-27.00% |
| Butyloctyl salicylate | 32-36% | | | 23.00-27.00% |
| Triethoxycaprylylsilane | 1-2% | 2% | 0.50-2.00% | 0.50-1.50% |
| TEA Oleth-3 Phosphate | 1-3% | 2% | | |
| C12-15 Alkyl Benzoate | | | 45-50% | |
| Polyhydroxystearic acid | | | 2.5-3.5% | |

TABLE 4

Sunscreen Formulations Comprising Zinc Oxide/Formula (I) Dispersions from Table 3.

| | Formulation | | | | | |
|---|---|---|---|---|---|---|
| | 1 (control) | 2 | 3 | 4 | 5 | 6 |
| Butyloctyl salicylate | | | 3.4% | 1.7% | | 3.2% |
| C12-C15 alkyl benzoates | | 4.7% | | | | |
| Ethylhexyl methoxycrylene (SOLASTAY ™ $S_1$) | 3.4% | | | 1.7% | 3.4% | 3.2% |
| ZnO (Z-Cote HP1) | | 6.2% | 6.2% | 6.2% | 6.2% | 6.2% |
| SPF | 4 | 5 | 7 | 8 | 15* | 16 |
| UVA-PF | 3 | 4 | 4 | 5 | 9* | 9 |

*validated in vivo

TABLE 5

Compositions of the Zinc Oxide/Formula (I) Sunscreen Formulations from Table 4.

| INGREDIENT INCI Name (Trade Name, Supplier) | Formulation | | | | | |
|---|---|---|---|---|---|---|
| | 1 | 2 | 3 | 4 | 5 | 6 |
| Water (distilled deionized) | 75.80% | 68.30% | 69.20% | 69.20% | 69.20% | 66.40% |
| Disodium EDTA (Versene ™ NA, Dow Chemical) | 0.05% | 0.05% | 0.05% | 0.05% | 0.05% | 0.05% |
| Xanthan Gum (Rhodicare ® XC, Rhodia) | 0.35% | 0.35% | 0.35% | 0.35% | 0.35% | 0.35% |
| Glycerin (Superol ™ K, Glycerine 99.7% USP/FCC Kosher, P&G Chemicals) | 5.00% | 5.00% | 5.00% | 5.00% | 5.00% | 5.00% |
| Methylparaben (CoSept ™ M, HallStar) | 0.20% | 0.20% | 0.20% | 0.20% | 0.20% | 0.20% |
| Ethylparaben (CoSept ™ E, HallStar) | 0.10% | 0.10% | 0.10% | 0.10% | 0.10% | 0.10% |
| PEG-150 Stearate (HallStar ® PEG 6000 MS, HallStar) | 2.10% | 2.10% | 2.10% | 2.10% | 2.10% | 2.10% |
| Glyceryl Stearate (and) PEG-100 Stearate (HallStar ® GMS SE/AS, HallStar) | 12.00% | 12.00% | 12.00% | 12.00% | 12.00% | 12.00% |
| Cetyl Alcohol (HallStar ® CO-1695 Cetyl Alc, HallStar) | 1.00% | 1.00% | 1.00% | 1.00% | 1.00% | 1.00% |
| Zinc Oxide (Z-Cote HP1, BASF) | | 6.20% | 6.20% | 6.20% | 6.20% | 6.20% |
| TEA Oleth-3 phosphate | | | 0.20% | | 0.20% | |
| Triethoxycaprylylsilane | | | 0.20% | | 0.20% | 0.20% |
| C12-15 alkyl benzoates | | 4.70% | | | | |
| Ethylhexyl methoxycrylene (SOLASTAY ™ $S_1$) | 3.40% | | | 1.70% | 3.40% | 3.20% |
| Butyloctyl salicylate | | | 3.40% | 1.70% | | 3.20% |
| SPF (In vitro) | 4 | 5 | 7 | 8 | 15 | 16 |
| PFA (In vitro) | 3 | 4 | 4 | 5 | 9 | 9 |
| SPF (In vivo) | | | | | 15 | |
| PFA (In vivo) | | | | | 9 | |

Example 2

Formulations of Titanium Dioxide with a Formula (I) Carrier

Titanium dioxide dispersions using ethylhexyl methoxycrylene (SOLASTAY™ $S_1$), butyloctyl salicylate (control), or C12-15 alkyl benzoate (control) as carriers were supplied by either Dynamic Dispersions LLC "DCI" or Kobo Products "Kobo" and formulated as shown in Table 6. The titanium dioxide particles were coated with either triethoxycaprylylsilane or alumina/methicone.

Sunscreens were formulated comprising 7% to 10% of the titanium dioxide dispersions of Table 6 and the SPF and UVA-PF values were determined as shown in Table 7. Control sunscreen formulations comprising dispersions of titanium dioxide and either butyloctyl salicylate or C12-C15 alkyl benzoates as the carrier had low SPF and UVA-PF values. Control sunscreen formulations comprising ethylhexyl methoxycrylene (SOLASTAY™ $S_1$) and no titanium dioxide also had low SPF and UVA-PF values. However, sunscreen formulations comprising dispersions of titanium dioxide with ethylhexyl methoxycrylene (SOLASTAY™ $S_1$) as the carrier had significantly higher SPF and UVA-PF values. The exact compositions of the titanium dioxide sunscreen formulations of Table 7 are shown in Table 8.

TABLE 6

Dispersions of Titanium Dioxide Using a Formula (I) Carrier

| Ingredients | Dispersion | | | |
|---|---|---|---|---|
| | D-5 | D-6 | D-7 | D-8 |
| Titanium Dioxide | 42-45% | 42-45% | 38.13% | 29.00-33.00% |
| Ethylhexyl methoxycrylene (SOLASTAY ™ $S_1$) | | 40% | | 26.50-3-.50% |
| Butyloctyl salicylate | 47-50% | 43% | | 26.50-30.50% |
| Triethoxycaprylylsilane | 1-2% | 1-2% | | |
| TEA Oleth-3 Phosphate | 3-6% | 3-6% | | |
| C12-15 Alkyl Benzoate | | | 45.00-50.00% | |
| Polyhydroxystearic acid | | | 1.00-5.00% | 2.00-4.00% |
| Alumina | | | 5.65-9.65% | 5.00-7.00% |
| Methicone | | | 1.85-5.85% | 2.00-3.50% |

TABLE 7

Sunscreen Formulations Comprising Titanium Dioxide/Formula (I) Dispersions from Table 6.

| | Formulation | | | | |
|---|---|---|---|---|---|
| | 1 (control) | 7 | 8 | 9 | 10 |
| Butyloctyl salicylate | | 3.4% | | 3.0% | 2.8% |
| C12-C15 alkyl benzoates | | | 3.8% | | |
| Ethylhexyl methoxycrylene (SOLASTAY ™ $S_1$) | 3.4% | | | 2.8% | 2.8% |
| Titanium Dioxide | | 3.1% | 3.1% | 3.1% | 3.1% |

TABLE 7-continued

Sunscreen Formulations Comprising Titanium Dioxide/Formula (I) Dispersions from Table 6.

| | Formulation | | | | |
|---|---|---|---|---|---|
| | 1 (control) | 7 | 8 | 9 | 10 |
| Surface Treatment | | Triethoxy-caprylylsilane | $Al_2O_3$, methicone | Triethoxy-caprylylsilane | $Al_2O_3$, methicone |
| SPF | 4 | 6 | 6 | 16 | 13 |
| UVA-PF | 3 | 2 | 2 | 5 | 4 |

TABLE 8

Compositions of the Titanium Dioxide/Formula (I) Sunscreen Formulations from Table 7.

| | Formulation | | | | |
|---|---|---|---|---|---|
| INGREDIENT INCI Name (Trade Name, Supplier) | 1 | 7 | 8 | 9 | 10 |
| Water (distilled deionized) | 75.80% | 72.20% | 71.10% | 69.80% | 69.30% |
| Disodium EDTA (Versene ™ NA, Dow Chemical) | 0.05% | 0.05% | 0.05% | 0.05% | 0.05% |
| Xanthan Gum (Rhodicare ® XC, Rhodia) | 0.35% | 0.35% | 0.35% | 0.35% | 0.35% |
| Glycerin (Superol ™ K, Glycerine 99.7% USP/FCC Kosher, P&G Chemicals) | 5.00% | 5.00% | 5.00% | 5.00% | 5.00% |
| Methylparaben (CoSept ™ M, HallStar) | 0.20% | 0.20% | 0.20% | 0.20% | 0.20% |
| Ethylparaben (CoSept ™ E, HallStar) | 0.10% | 0.10% | 0.10% | 0.10% | 0.10% |
| PEG-150 Stearate (HallStar ® PEG 6000 MS, HallStar) | 2.10% | 2.10% | 2.10% | 2.10% | 2.10% |
| Glyceryl Stearate (and) PEG-100 Stearate (HallStar ® GMS SE/AS, HallStar) | 12.00% | 12.00% | 12.00% | 12.00% | 12.00% |
| Cetyl Alcohol (HallStar ® CO-1695 Cetyl Alc, HallStar) | 1.00% | 1.00% | 1.00% | 1.00% | 1.00% |
| TEA Oleth-3 phosphate | | 0.37% | | 0.37% | |
| Titanium dioxide | | 3.10% | 3.10% | 3.10% | 3.10% |
| Alumina | | | 0.62% | | 0.60% |
| Polyhydroxystearic acid | | | 0.23% | | 0.30% |
| Triethoxycaprylylsilane | | 0.13% | | 0.13% | |
| Methicone | | | 0.35% | | 0.30% |
| C12-15 alkyl benzoates | | | 3.80% | | |
| Ethylhexyl methoxycrylene (SOLASTAY ™ $S_1$) | | | | 2.80% | 2.80% |
| Butyloctyl salicylate | 3.40% | 3.40% | | 3.40% | 2.80% |
| SPF (In vitro) | 4 | 6 | 6 | 16 | 13 |
| PFA (In vitro) | 3 | 2 | 2 | 5 | 4 |

Example 3

Synergistic Effect of Combining an Alkoxycrylene Compound with an Inorganic Particulate in a Dispersion The SPF and UVA-PF values of zinc oxide dispersions comprising the alkoxycrylene compound of Formula I were compared to zinc oxide dispersions comprising oxycrylene or to zinc oxide dispersions with a high dielectric constant. The synergies of these dispersions were then calculated and are shown in Table 9. Synergy is the magnitude of the SPF or UVA-PF value over the SPF or UVA-PF value that would be expected from purely an additive effect. The purely additive effect results from the addition of, for example, the SPF value of a dispersion comprising alkoxycrylene and no zinc oxide to the SPF value of a dispersion comprising only zinc oxide and no alkoxycrylene. Dispersions comprising the alkoxycrylene compound of Formula I combined with zinc oxide show astonishing +66% and +29% synergies for the SPF and UVA-PF values, respectively.

TABLE 9

Comparison of SOLASTAY ™ $S_1$ Dispersions with Octocrylene Dispersions and High Dielectric Constant Dispersions

| | | | | Comparison to Octocrylene | | Comparison to a High Dielectric Constant Dispersion | |
|---|---|---|---|---|---|---|---|
| | 11 Control | 12 Control | 13 Control | 14 Octocrylene Test | 15 SOLASTAY ™ $S_1$ Test | 16 OC/DMDA Test | 17 SOLASTAY ™ $S_1$ Test |
| C12-C15 alkyl benzoates | | 4.7% | | | | | |
| Butyloctyl salicylate | | | | | | | 3.2% |
| Octocrylene (OC) | 3.4% | | | 3.4% | | 3.2% | |
| Dimethyl capramide (DMDA) | | | | | 3.4% | 3.2% | |
| Ethylhexyl methoxycrylene (SOLASTAY ™ $S_1$) | | | 3.4% | | | | 3.2% |
| Zinc Oxide (Z-Cote HP1, BASF) | | 6.2% | | 6.2% | 6.2% | 6.2% | 6.2% |
| Dielectric Constant | | | | | | 12.9 | 8.6* |
| SPF | 7 | 5 | 4 | 14 | 15 | 12 | 15 |

TABLE 9-continued

Comparison of SOLASTAY ™ S₁ Dispersions with Octocrylene Dispersions and High Dielectric Constant Dispersions

|  | 11 Control | 12 Control | 13 Control | Comparison to Octocrylene | | Comparison to a High Dielectric Constant Dispersion | |
|---|---|---|---|---|---|---|---|
|  |  |  |  | 14 Octocrylene Test | 15 SOLASTAY ™ S₁ Test | 16 OC/DMDA Test | 17 SOLASTAY ™ S₁ Test |
| UVA-PF SYNERGY | 2 | 4 | 3 | 5 +16% SPF −16% PFA | 9 +66% SPF +29% PFA | 4 +0% SPF −33% PFA | 9 +66% SPF +29% PFA |

*Applies to a mixture of butyloctyl salicylate and SOLASTAY ™ S₁. SOLASTAY ™ S₁ alone is 12.9.

The invention claimed is:

1. A photostabilized sunscreen or dermatological composition for protecting skin from UV radiation comprising an inorganic particulate material in an amount of about 1 wt % to about 70 wt %, a compound of formula (I) in an amount of about 1 wt % to about 70 wt %, a particulate material coating material in an amount of about 0 wt % to about 10 wt %, and a dispersing agent for the particulate material in an amount of about 0 wt % to about 10 wt %, based on the total weight of the composition,

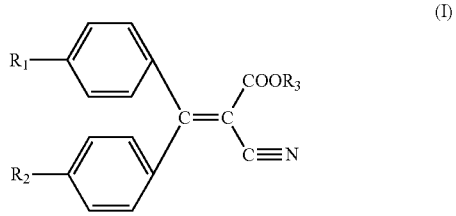

wherein one of $R_1$ and $R_2$ is a straight or branched chain $C_1$-$C_{30}$ alkoxy radical, and the non-alkoxy $R_1$ or $R_2$ is hydrogen; and $R_3$ is a straight or branched chain $C_1$-$C_{30}$ alkyl radical.

2. The composition of claim 1, wherein $R_1$ is methoxy and $R_2$ is hydrogen.

3. The composition of claim 1, wherein $R_2$ is methoxy and $R_1$ is hydrogen.

4. The composition of claim 1, wherein $R_3$ is a $C_2$-$C_{20}$ straight chain or branched alkyl.

5. The composition of claim 1, wherein the compound of formula (I) is present in an amount in the weight range of about 10% to about 40%, based on the total weight of the composition.

6. The composition of claim 1, wherein the particulate material is a metal oxide.

7. The composition of claim 6, wherein the metal oxide is micronized.

8. The composition of claim 7, wherein the micronized metal oxide is an oxide of a metal selected from the group consisting of titanium, zinc, iron, zirconium, silicon, manganese, aluminum, cerium, and mixtures thereof.

9. The composition of claim 8, wherein the micronized metal oxide is zinc oxide.

10. The composition of claim 8, wherein the micronized metal oxide is titanium dioxide.

11. The composition of claim 10, wherein the micronized titanium dioxide is doped with manganese.

12. The composition of claim 7, wherein the micronized metal oxide has a particle size of less than 300 nm.

13. The composition of claim 12, wherein the micronized metal oxide has a particle size of 10 to 200 nm.

14. The composition of claim 1, wherein the particulate material is barium sulfate.

15. The composition of claim 1, wherein the particulate material is present in an amount of about 20 wt % to about 65 wt %, based on the total weight of the composition.

16. The composition of claim 15, wherein the particulate material is present in an amount of about 45 wt % to about 60 wt %, based on the total weight of the composition.

17. The composition of claim 1, wherein the coating material for the particulate material is in an amount of about 1 wt % to about 10 wt %, based on the total weight of the composition.

18. The composition of claim 17, wherein the coating material for the particulate material is selected from the group consisting of dimethylpolysiloxane, triethyoxycaprylylsilane, methylpolysiloxane, simethicone, ethylhexyl hydroxystearate benzoate, cyclomethicone, aluminum oxide, aluminum hydroxide, aluminum oxide hydrate, sodium hexametaphosphate, sodium metaphosphate, silicon dioxide, iron oxide, polyols, amines, alkanolamines, aluminum stearate, stearic acid, lauric acid, alginic acid, silicone, octyltrimethylsilane, and combinations thereof.

19. The composition of claim 1, wherein the dispersing agent for the particulate material is in an amount of about 1 wt % to about 10 wt %, based on the total weight of the composition.

20. The composition of claim 1 comprising the inorganic particulate material in an amount of about 0.1 wt % to about 25 wt % and the compound of formula (I) in an amount of about 0.1 wt % to about 15 wt %, based on the total weight of the composition.

21. The composition of claim 20, wherein the composition includes one or more oxidation-sensitive or UV-sensitive ingredients selected from the group consisting of retinoid compounds, carotenoid compounds, lipoic acid and derivatives thereof, vitamin E and derivatives thereof, vitamin F and derivatives thereof, and dioic acid in an amount from about 0.0001 wt % to about 10 wt %, based on the total weight of the composition.

22. The composition of claim 21, wherein the oxidation-sensitive or UV-sensitive ingredients are selected from the group consisting of coenzyme Q10 and vitamin A and derivatives thereof.

23. The composition of claim 20, wherein the composition includes a hydrophilic active ingredient selected from the group consisting of biotin, carnitine and derivatives, folic acid, pyridoxine, niacinamide, polyphenols, ascorbic acid and derivatives, Hamamelis, Aloe Vera, panthenol, and amino acids in an amount from about 0.0001% to about 10% by weight, based on the total weight of the composition.

24. The composition of claim 20, wherein the inorganic particulate material is present in the composition in an amount of about 2 wt % to about 8 wt % and the compound of formula (I) is present in the composition in an amount of about 1 wt % to about 7 wt %, based on the total weight of the composition.

25. A method of protecting skin from UV radiation comprising applying a photostabilized sunscreen or dermatological composition to the skin comprising an inorganic particulate material in an amount of about 1 wt % to about 70 wt %, a compound of formula (I) in an amount of about 1 wt % to about 70 wt %, a particulate material coating material in an amount of about 0 wt % to about 10 wt %, and a dispersing agent for the particulate material in an amount of about 0 wt % to about 10 wt %, based on the total weight of the composition,

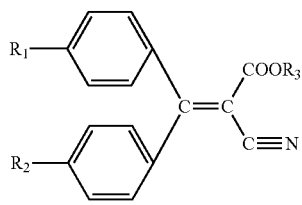
(I)

wherein one of $R_1$ and $R_2$ is a straight or branched chain $C_1$-$C_{30}$ alkoxy radical, and the non-alkoxy $R_1$ or $R_2$ is hydrogen; and $R_3$ is a straight or branched chain $C_1$-$C_{30}$ alkyl radical.

26. The method of claim 25, further including one or more photoactive compounds selected from the group consisting of p-aminobenzoic acid and salts and derivatives thereof; anthranilate and derivatives thereof; dibenzoylmethane and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone naphtholsulfonate and salts and derivatives thereof; benzalacetophenone naphtholsulfonate and salts and derivatives thereof; dihydroxy-naphthoic acid and salts thereof; o-hydroxydiphenyldisulfonate and salts and derivatives thereof; p-hydroxydiphenyldisulfonate and salts and derivatives thereof; coumarin and derivatives thereof; diazole derivatives; quinine derivatives and salts thereof; quinoline derivatives; hydroxyl-substituted benzophenone derivatives; dialkyl naphthalate ester derivatives; hydroxybenzophenone derivatives, methoxy-substituted benzophenone derivatives; uric acid derivatives; vilouric acid derivatives; tannic acid and derivatives thereof; hydroquinone; benzophenone derivatives; 1,3,5-triazine derivatives; disodium phenyl dibenzimidazole and salts thereof; terephthalylidene dicamphor sulfonic acid and salts and derivatives thereof; methylene bis-benzotriazolyl tetramethylbutylphenol and salts and derivatives thereof; bis-ethylhexyloxyphenol methoxyphenyl triazine and salts, diethylamino hydroxyl benzoyl and derivatives thereof; phenylbenzimidazole sulfonic acid and salts thereof; terephthalylidene dicamphor sulfonic acid and salts thereof; and combinations of the foregoing.

27. The method of claim 26, wherein the one or more photoactive compounds is selected from group consisting of a dibenzoylmethane derivative; a cinnamate ester; an ester of an alkoxycinnamate, an octyl salicylate, and a combination thereof.

28. The method of claim 27, wherein the dibenzoylmethane derivative comprises butyl methoxy dibenzoylmethane.

29. The method of claim 27, wherein the cinnamate ester is selected from the group consisting of 2-ethylhexyl p-methoxycinnamate; isoamyl p-methoxycinnamate; and a combination thereof.

30. The method of claim 25 further including 0.1 to 10 wt. % of a triplet quencher selected from the group consisting of octocrylene, methyl benzylidene camphor, diethylhexyl 2,6-naphthalate, and combinations thereof.

31. The method of claim 25, further comprising at least one UV filter substance selected from the group consisting of UV-A filters, UV-B filters, broad-band filters, triazines, benzotriazoles, latex particles, organic pigments, inorganic pigments, and mixtures thereof.

32. The method of claim 31, wherein the UV filter substance is a benzotriazole compound having the structure

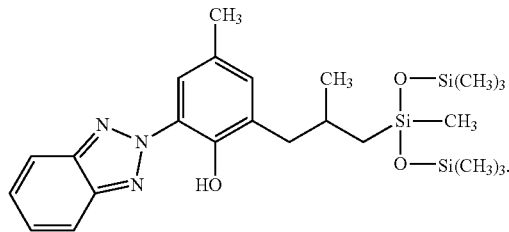

* * * * *